United States Patent
Yoon

[11] Patent Number: 5,993,470
[45] Date of Patent: Nov. 30, 1999

[54] UNIVERSAL HANDLE FOR MEDICAL INSTRUMENTS

[76] Inventor: InBae Yoon, 2101 Highland Ridge Dr., Phoenix, Md. 21131

[21] Appl. No.: 08/362,223

[22] Filed: Dec. 23, 1994

Related U.S. Application Data

[63] Continuation-in-part of application No. 07/945,177, Sep. 15, 1992.

[51] Int. Cl.⁶ ...................................................... A61M 5/00
[52] U.S. Cl. ................................ 606/185; 606/1; 604/165
[58] Field of Search ..................................... 128/751, 752, 128/753, 754; 604/95, 158, 162, 163, 164, 165, 170, 272, 274, 280, 169; 606/167, 171, 185, 1

[56] References Cited

U.S. PATENT DOCUMENTS

| | | |
|---|---|---|
| 4,535,773 | 8/1985 | Yoon . |
| 5,116,353 | 5/1992 | Green . |
| 5,152,754 | 10/1992 | Plyley et al. . |
| 5,158,552 | 10/1992 | Borgia et al. . |
| 5,226,426 | 7/1993 | Yoon . |
| 5,290,243 | 3/1994 | Chodorow . |
| 5,290,304 | 3/1994 | Storace . |
| 5,292,310 | 3/1994 | Yoon . |
| 5,295,993 | 3/1994 | Green . |
| 5,312,354 | 5/1994 | Allen et al. . |
| 5,318,580 | 6/1994 | Gresl . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,346,459 | 9/1994 | Allen . |
| 5,350,393 | 9/1994 | Yoon . |
| 5,356,421 | 10/1994 | Castro . |
| 5,360,405 | 11/1994 | Yoon . |
| 5,376,082 | 12/1994 | Phelps . |
| 5,382,255 | 1/1995 | Castro et al. . |
| 5,383,881 | 1/1995 | Green et al. . |

OTHER PUBLICATIONS

Manufacturer's brochure for "Dial Push–Pull Gauge Model DPP" by Chatillon, one page. Author and Date Unknown.

*Primary Examiner*—Guy V. Tucker

[57] ABSTRACT

A universal handle for medical instruments includes a first member movably disposed within a housing for detachably mounting a first medical instrument, a bias member for moving the first member toward a retracted or extended position near one end of the housing, a locking mechanism for engaging the first member in the retracted or extended position to prevent the bias member from moving the first member into the retracted or extended position, and a releasing mechanism including an operating member movable in response to a reduction in force acting on a component of the handle for triggering release of the locking mechanism to permit the bias member to move the first member to the retracted or extended position. A second member for detachably mounting a second medical instrument can be held stationary relative to the housing or can be movably disposed within the housing between extended and retracted positions. Opposite ends of the universal handle can be configured to provide at least one of a retracting and a protruding function as desired.

59 Claims, 16 Drawing Sheets

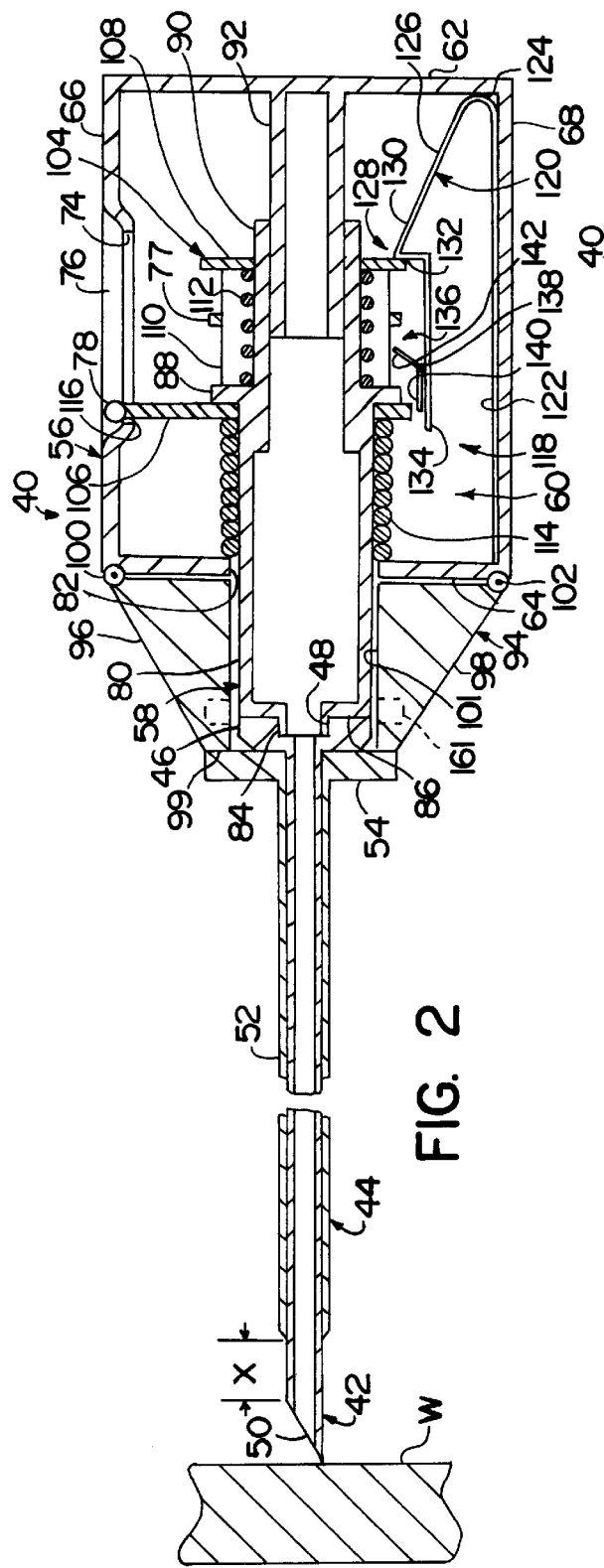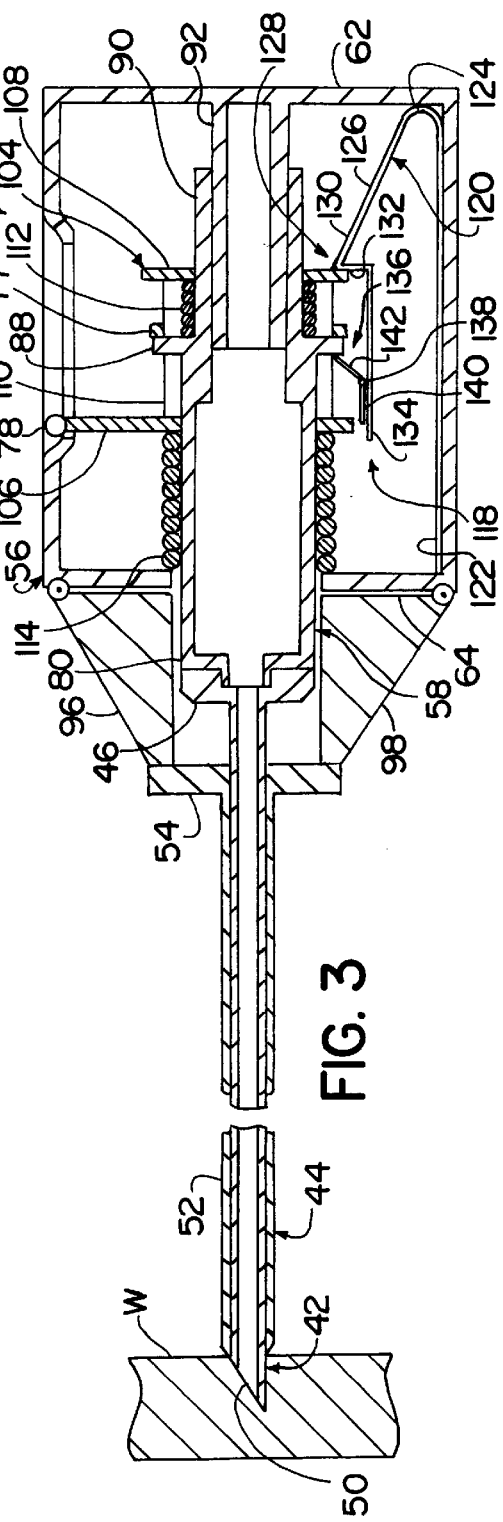

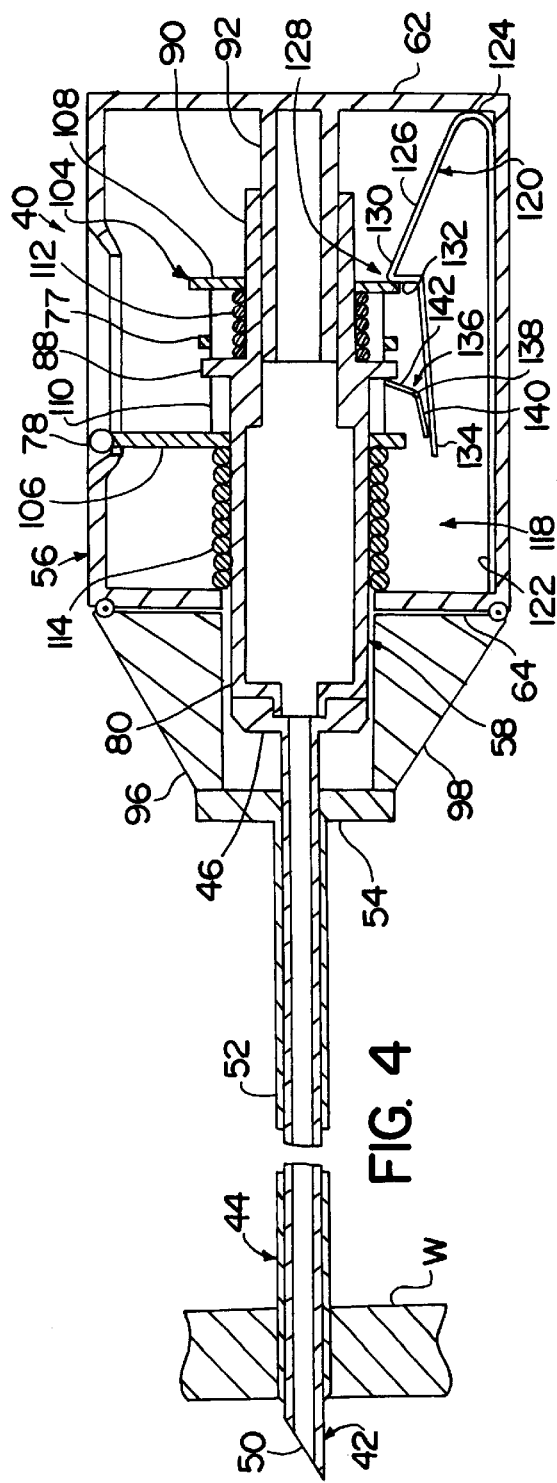
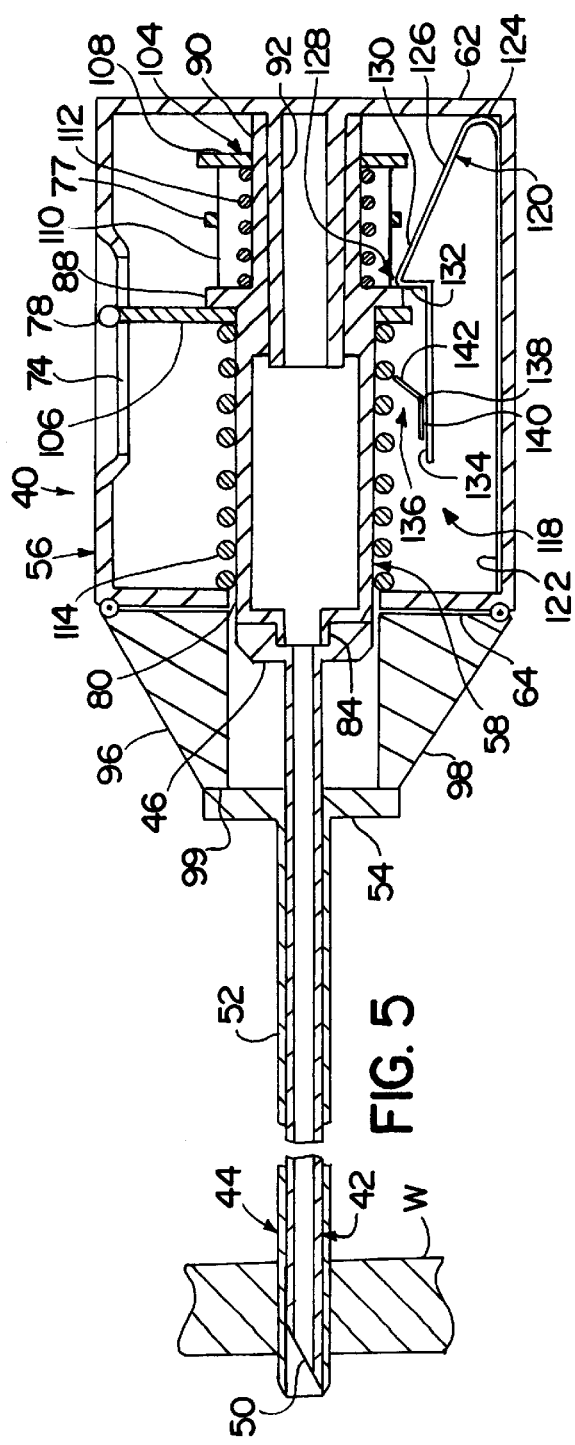

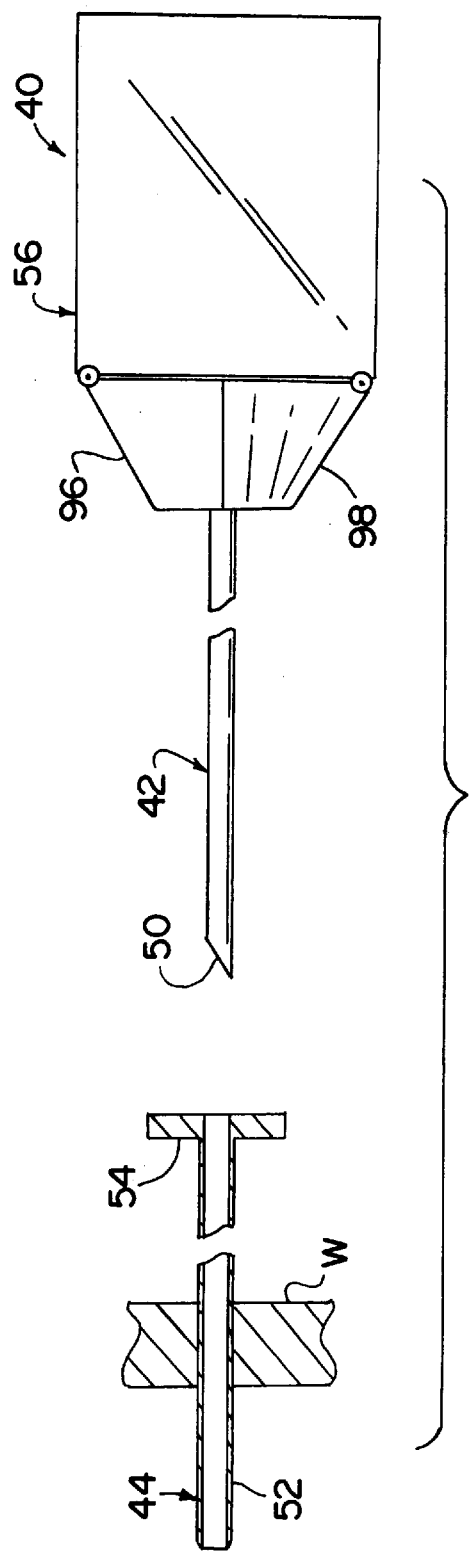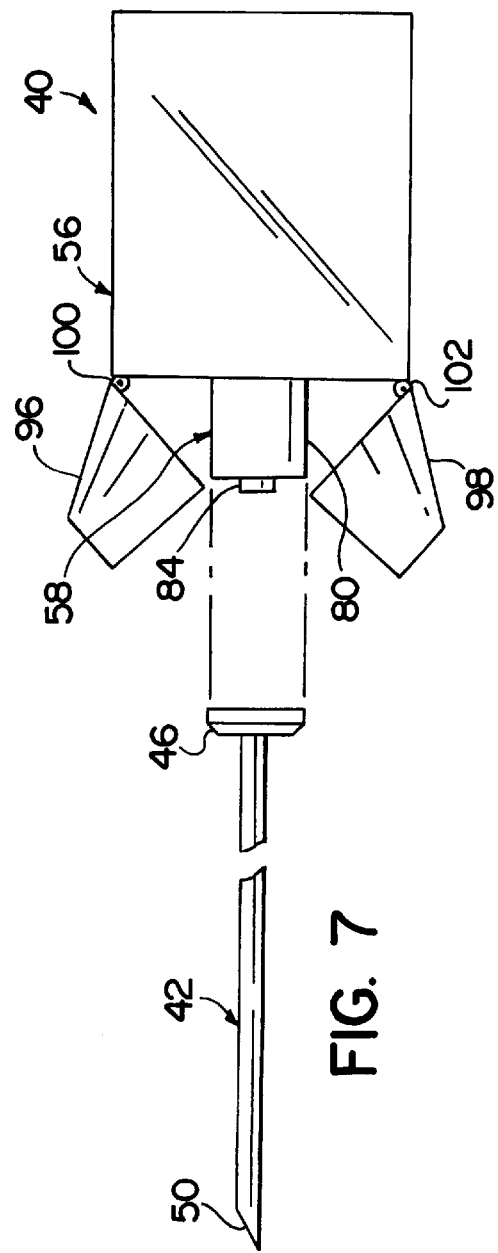
FIG. 6
FIG. 7

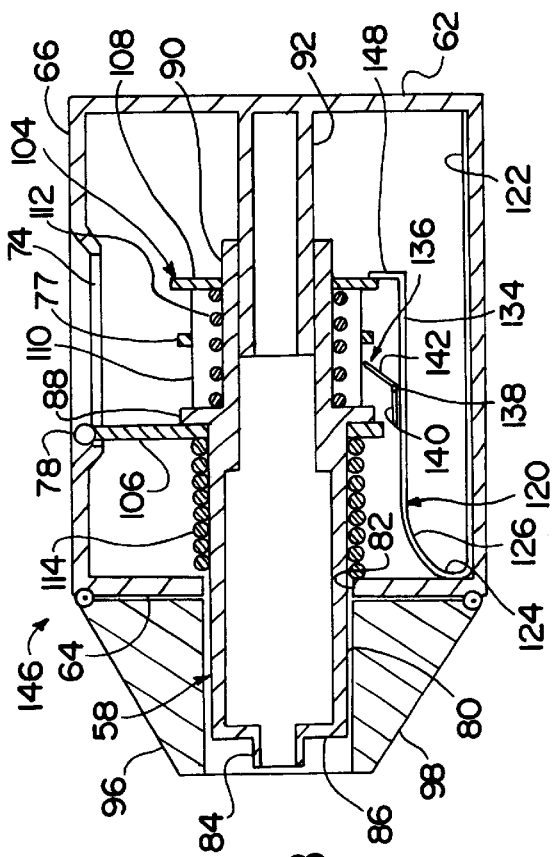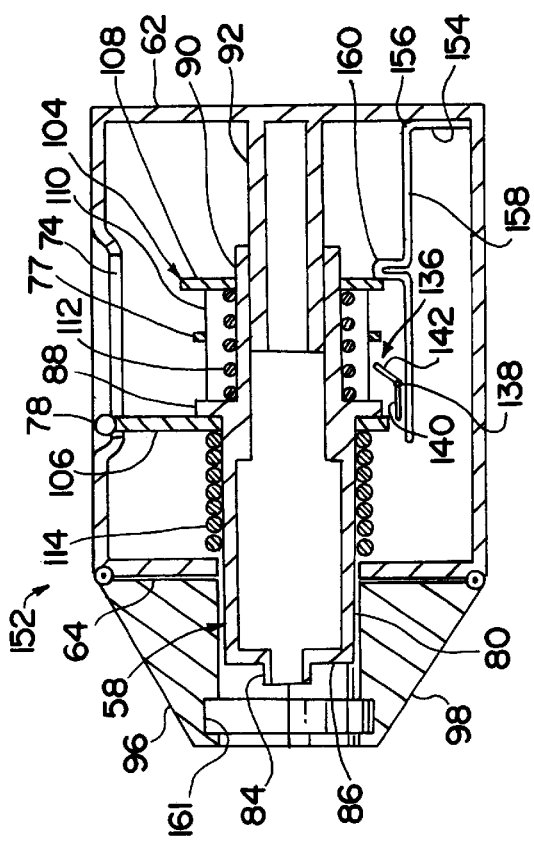

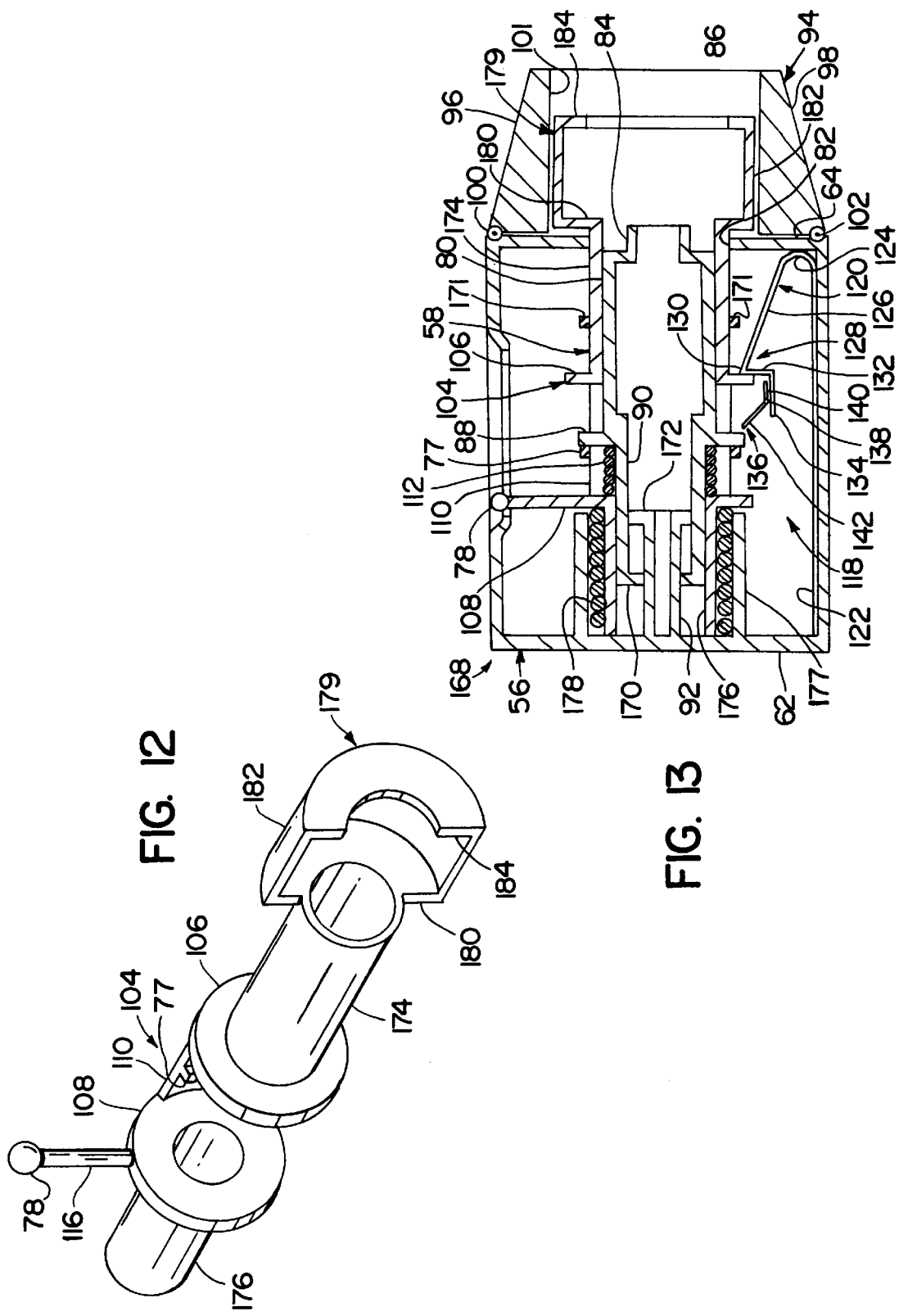

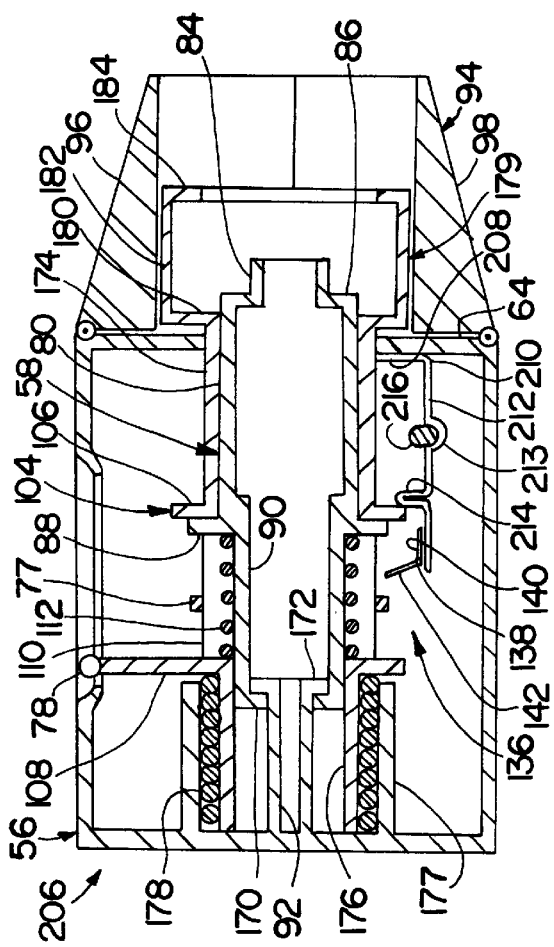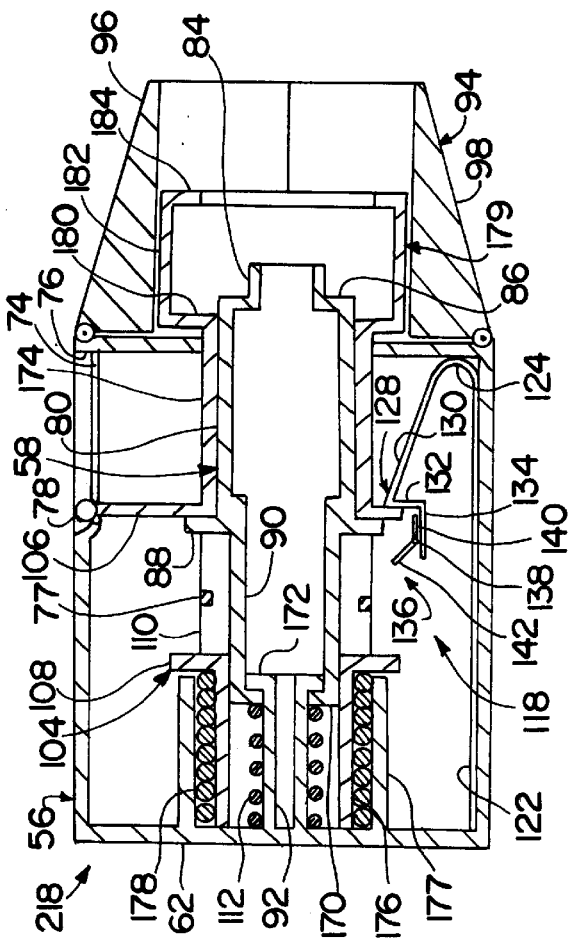

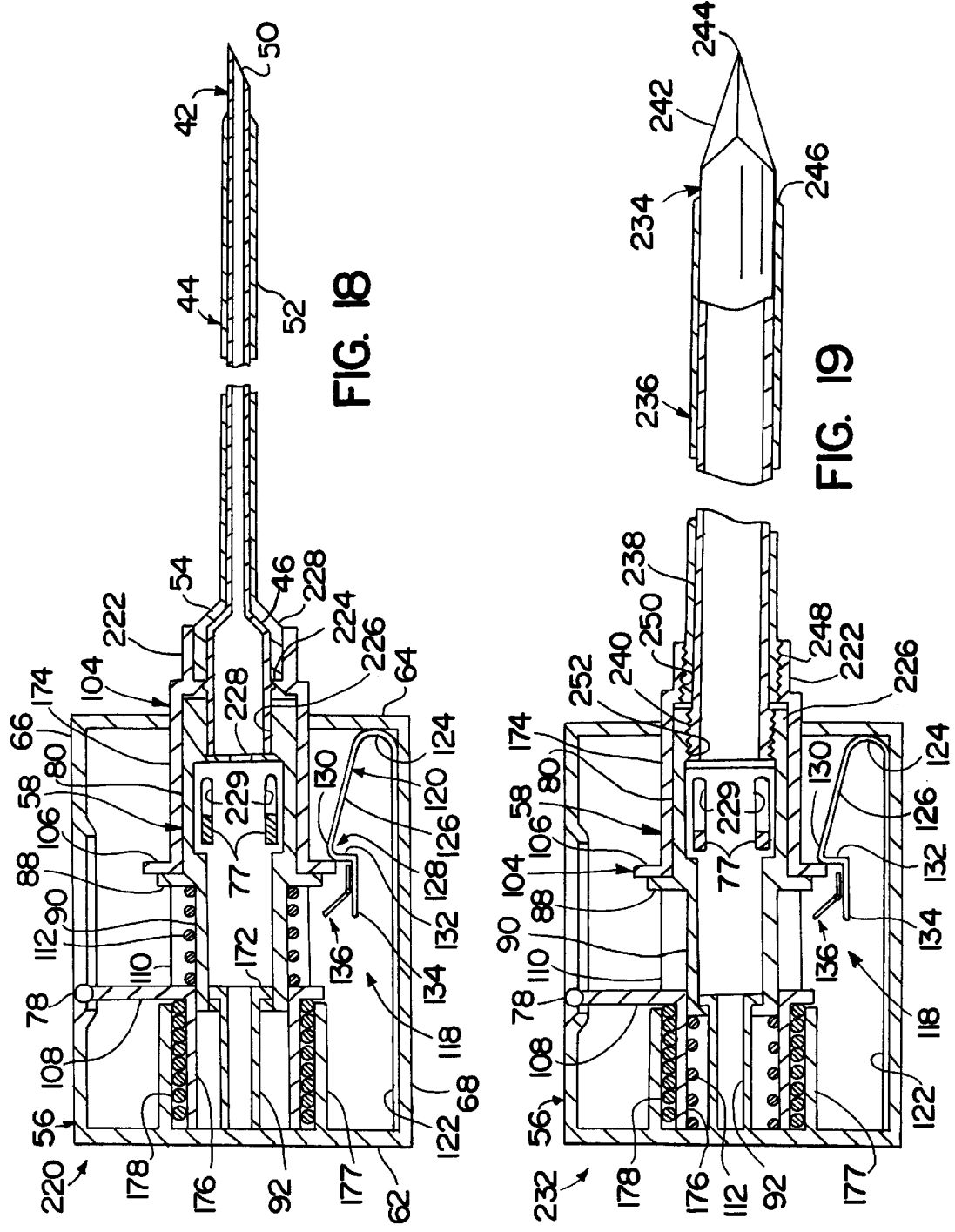

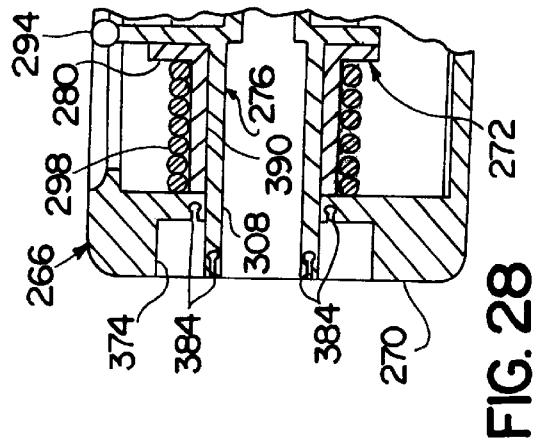
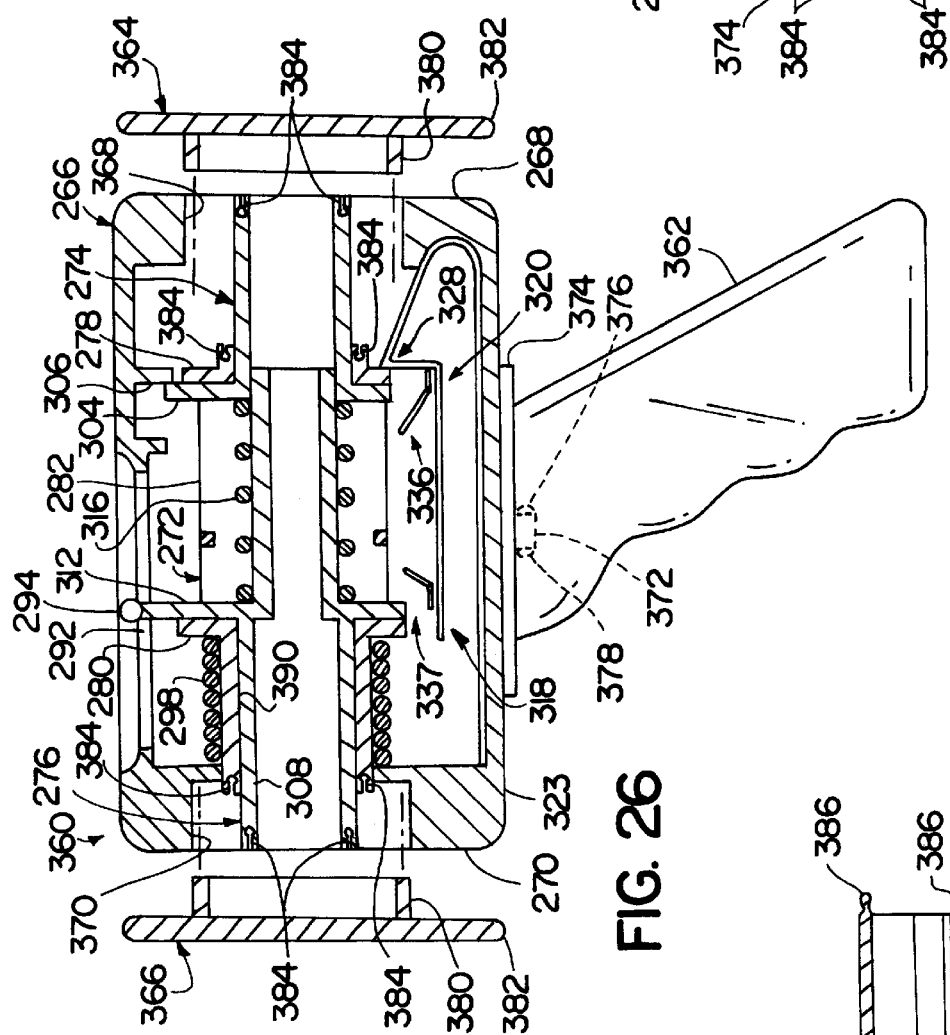
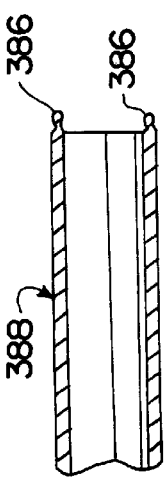

UNIVERSAL HANDLE FOR MEDICAL INSTRUMENTS

CROSS-REFERENCE TO RELATED APPLICATIONS

This application is a continuation-in-part of copending patent applications Ser. No. 07/945,177, filed Sep. 15, 1992, still pending.

BACKGROUND OF THE INVENTION

1. Field of the Invention

The present invention relates to medical procedures and instruments and, more particularly, to a universal handle providing a retracting and/or a protruding function for medical instruments.

2. Brief Description of the Related Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laproscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring-biased to protrude beyond the tip of the penetrating member in response to the reduced force on the distal end of the safety member upon entering into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

A disadvantage of safety penetrating instruments in general is that relatively complex mechanisms are required to retract a penetrating member or protrude a safety member such that integral construction of the safety penetrating instruments requires sterilization or disposal of the entire unit after use, significantly increasing the cost of utilizing such instruments. Another disadvantage of the prior art instruments is that penetrating components, such as the penetrating member and safety member, are not interchangeable between penetrating instruments. As such, if the type or size of a penetrating component is not correct for the application, an entirely new safety penetrating instrument must be selected. Moreover, there is no flexibility to selectively match a particular penetrating component with a particular protruding or retracting power.

SUMMARY OF THE INVENTION

Accordingly, it is a primary object of the present invention to overcome the above-mentioned disadvantages of the prior art and to reduce the cost of using medical instruments by locating retracting and/or protruding mechanisms within a universal handle configured to detachably mount the medical instruments.

It is another object of the present invention to facilitate disposal of medical instruments and reuse of mechanisms used for retracting and/or protruding the medical instruments in order to reduce the cost of using the medical instruments.

Yet another object of the present invention is to standardize protruding and/or retracting mechanisms disposed within a universal handle configured to detachably mount a variety of medical instruments.

Still another object of the present invention is to utilize opposite ends of a universal handle for selectively protruding and/or retracting medical instruments.

Some of the advantages of the universal handle of the present invention are that, once use of a medical instrument has been exhausted, the medical instrument can be easily and safely removed from the universal handle such that the universal handle can subsequently be used in conjunction with another medical instrument. Thus, if the medical instruments are to be discarded, it is not necessary to discard the universal handle that contains retracting and/or protruding mechanisms. Such a universal handle greatly minimizes the cost of using medical instruments because only the instruments themselves need be thrown away without disposing of the universal handle that contains the retracting and/or protruding mechanisms. Thus, the universal handle of the present invention can be used many times over without the need for disposal. Also, by utilizing opposite ends of the universal handle to selectively protrude or retract medical instruments, the number of handles required to be kept on hand for performing the above functions is reduced.

The present invention is generally characterized in a universal handle for medical instruments including a housing having proximal and distal ends; a first member disposed within the housing for detachably mounting a first medical instrument, the first member being movable between an extended position proximate the distal end of the housing and a retracted position proximate the proximal end of the housing; retracting means for moving the first member proximally toward the retracted position; locking means for engaging the first member in the extended position to prevent the retracting means from moving the first member into the retracted position; and releasing means including an operating member movable distally in response to a reduction in force acting on a component of the handle for triggering release of the locking means to permit the retracting means to move the first member to the retracted position.

Another aspect of the present invention is generally characterized in a universal handle for medical instruments including a housing having proximal and distal ends; a first member disposed within the housing for detachably mounting a first medical instrument, the first member being movable between a retracted position proximate the proximal end of the housing and an extended protruding position proximate the distal end of the housing; extending means for moving the first member from the retracted position to the extended protruding position; locking means for engaging the first member in the retracted position to prevent the extending means from moving the first member into the extended position; and releasing means including an operating member carried by a component of the handle for triggering release of the locking means in response to a reduction in force acting on the component so as to permit the extending means to move the first member to the extended position.

Yet another aspect of the present invention is characterized in a universal handle for medical instruments including a housing having first and second opposed ends; a first member disposed within the housing and having first and second opposed ends, the first end having a configuration for mounting a first medical instrument, the first member being movable between a rest position proximate the first end of the housing and a retracted position proximate the second end of the housing; a second member disposed within the housing and having first and second opposed ends, the second end of the second member having a configuration for detachably mounting a second medical instrument, the second member being movable between an extended position proximate the second end of the housing and a retracted position proximate the first end of the housing; bias means for biasing the first and second members toward the first end of the housing; locking means for locking the first member in the retracted position and the second member in the extended position; and releasing means including an operating member carried by a component of the handle for triggering release of the locking means in response to a reduction in force acting on the component so as to permit the bias means to move the first and second members toward the first end of the housing.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 2 is a side view, partly in section, of the universal handle of FIG. 1 taken through line 2—2.

FIGS. 3–7 are side views, partly in section, illustrating use of the universal handle of FIG. 1.

FIG. 8 is a side view, partly in section, of a modification of the universal handle of the present invention.

FIG. 9 is a side view, partly in section, of another modified universal handle according to the present invention.

FIG. 12 is an enlarged perspective view of a rail member for use with the universal handle of FIG. 11.

FIGS. 13 and 14 are side views, partly in section, illustrating operation of the universal handle of FIG. 11.

FIG. 16 is a side view, partly in section, of another modification of the universal handle according to the present invention.

FIG. 17 is a side view, partly in section, of yet another modification of the universal handle according to the present invention.

FIG. 18 is a side view, partly in section, of another modified universal handle according to the present invention together with a needle and a cannula for use with the universal handle.

FIG. 19 is a side view, partly in section, of another modification of a universal handle in accordance with the present invention together with a penetrating member and a portal sleeve for use with the universal handle.

FIG. 26 is a side view, partly in section, of another modification of a universal handle according to the present invention.

FIG. 27 is a fragmentary cross-sectional view of the proximal end of a medical instrument for use with the universal handle of FIG. 26.

FIG. 28 is a fragmentary side view, partly in section, of a modification of the universal handle of FIG. 26.

DETAILED DESCRIPTION OF THE PREFERRED EMBODIMENTS

The universal handle of the present invention is described hereinafter for use in holding medical instruments of the type used to form portals in anatomical cavity walls for the introduction of fluids and various surgical and diagnostic instruments into the cavity. It is understood, however, that the universal handle and method of the present invention can be used to hold any type of medical instrument as well as to provide a retracting and/or extending or protruding function to any medical instruments held. By "medical instrument," therefore, is meant any type of implement having a configuration useful for medical purposes including, for example, penetrating members such as trocars and needles, cannulae such as portal sleeves and catheters, safety shields and probes, cutting members such as blades, hooks, biopsy tools and viewing instruments such as endoscopes.

Figure 1:
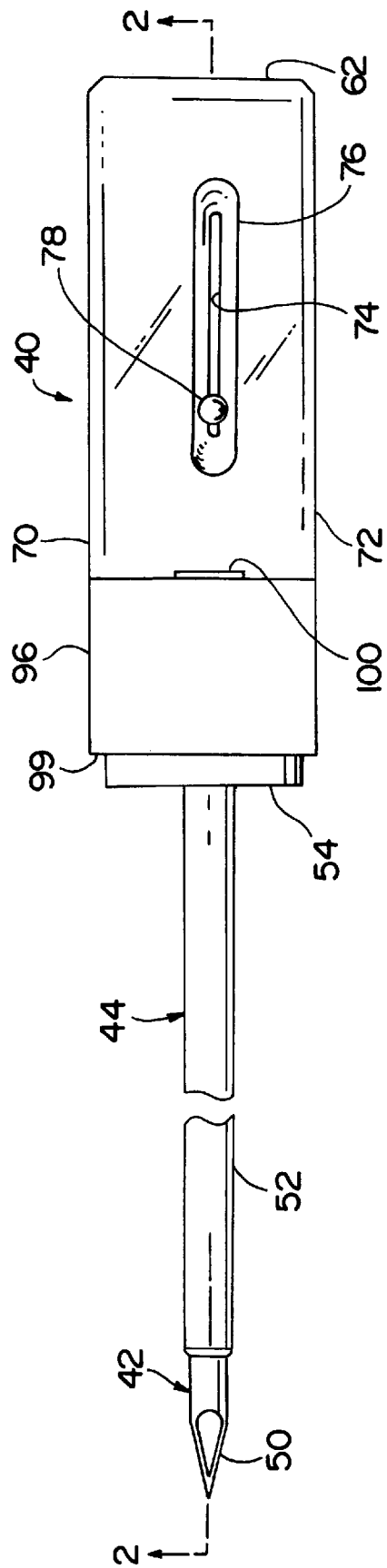
FIG. 1 is a top view of a universal handle according to the present invention.

A handle 40 according to the present invention is illustrated in FIGS. 1 and 2 carrying a needle 42 for penetrating a wall of an anatomical cavity and a catheter 44 slidable over the needle for placement in the anatomical cavity wall. As best seen in FIG. 2, needle 42 has a cylindrical base 46 at a proximal end with a central recess 48 formed therein and a beveled distal end 50. Catheter 44 includes an elongate tubular portion 52 with a round flange 54 at a proximal end. Needle 42 and catheter 44 are representative of the types of conventional medical instruments that can be used with the handle of the present invention. It will be appreciated, however, that medical instruments other than needles and catheters can be used.

Universal handle 40 according to the present invention includes a housing 56, a tubular mounting member 58 slidably disposed within the housing, and a retracting mechanism for locking the tubular member in an extended position within the housing and for releasing the tubular member to be moved proximally to a retracted position in response to a reduction in force acting on the tubular member.

Housing 56 can be made of any medically-acceptable material depending on the desirability of being sterilizable for reuse or disposable for single patient use and can have any desirable configuration to facilitate grasping by the user. The housing shown is generally rectangular with opposed proximal and distal end walls 62 and 64 disposed transverse of perpendicular to a longitudinal axis of the handle, spaced top and bottom walls 66 and 68, and laterally spaced sidewalls 70 and 72. A longitudinal slot 74 is formed at the bottom of an elongate, trough-like recess 76 defined in the housing top wall 66 to accommodate a knob 78 as will be described in more detail below.

Tubular member 58 includes a first cylindrical portion 80 extending through an opening 82 formed in the distal end wall 64 of the housing, a cylindrical nub 84 of decreased diameter carried on a distal face 86 of the first cylindrical portion, a round flange 88 carried or formed at a proximal end of the first cylindrical portion and a second cylindrical portion 90 of decreased diameter extending proximally from the flange. The second cylindrical portion 90 is telescopically fitted over a guide tube 92 extending from the proximal end wall 62 of the housing in longitudinal alignment with the opening 82 in the distal end wall 64 to permit sliding movement of the tubular member within the housing.

A collar or chuck 94 having a generally trapezoidal cross-section extends from distal end wall 64 and is split longitudinally to form opposed wedge-shaped jaws 96 and 98 which, when closed together, form a distal retaining surface 99 preventing proximal movement of the base of the catheter 44. A cylindrical bore 101 is defined between the closed jaws in axial alignment with the opening 82 in the distal end wall and is configured to guide medical instruments toward the distal end of the tubular member 58 and to align mating portions of the instruments with the cylindrical nub 84 thereby easing attachment. The first cylindrical portion 80 of the tubular member is telescopically received within the bore 101 and is slidingly movable therein. The jaws 96 and 98 are pivotally mounted on pins or hinges 100 and 102 secured to the housing at opposite ends of the distal end wall 64 so that the jaws can be rotated apart as shown in FIG. 7 to expose the distal end of the tubular member 58. The jaws are preferably spring-biased toward one another, for example using torsion springs (not shown). Alternatively, or in addition to being spring-biased toward one another the jaws can be held together in the closed condition by use of detents or any other suitable latching mechanism.

A rail member 104 is disposed in housing 56 and is generally U-shaped including a forward wall 106 disposed transverse of perpendicular to a longitudinal axis of the housing, a rearward wall 108 in configuration parallel to forward wall 106 and a side wall 110 transversely joining the forward and rearward rail member walls. Tubular member flange 88 is disposed between the rail member forward and rearward walls with the rail member forward wall 106 having an opening therein allowing passage therethrough by the first cylindrical portion 80 of the tubular member 58. The rail member forward and rearward walls are disposed parallel or substantially parallel to flange 88, and a bias member 112 is connected between flange 88 and the rail member rearward wall 108 to bias the tubular member distally. As shown, bias member 112 includes a helical coil spring disposed around the second cylindrical portion 90 of the tubular member and mounted in compression between flange 88 and the rail member rearward wall 108 to bias the tubular member distally causing flange 88 to abut the rail member forward wall 106. However, bias member 112 can include various other types of springs as well as other types of bias devices including compression springs, tension springs, torsion springs, pan springs, leaf springs, rubber, plastic or magnets, for example. Rail member forward wall 106 extends toward the top wall 66 of housing 56, and a retracting member 114 is mounted between the rail member forward wall 106 and the distal end wall 64 of housing 56 to bias the tubular member 58 in a proximal direction to a retracted position within the housing as will be explained further below. The retracting member 114 can include a helical coil spring mounted in compression between the rail member forward wall 106 and the distal end wall 64 of the housing as shown, or the retracting member can include any other type of spring or other bias devices as discussed above for bias member 112.

A post 116 extends upward from the rail member forward wall 106 through slot 74 in the housing top wall 66 to terminate at knob 78 positioned in the elongate, trough-like recess 76 formed in the housing top wall 66. Slot 74 and recess 76 extend longitudinally in parallel with the longitudinal axis of the handle 40. A stop 77 extends from the lateral side wall 110 of the rail-member and is disposed between the rail member forward and rearward walls to limit proximal movement of the tubular member flange 88 relative to the rail member.

A locking and releasing mechanism 118 for locking the tubular member 58 in an extended position proximate the distal end of the housing and for releasing the tubular member to allow the tubular member to move to a retracted position proximate the proximal end of the housing includes a latch or locking spring 120, made of a strip of resilient material, formed to have a substantially flat base 122 secured to the bottom wall 68 of housing 56 and a bend 124 joining the base 122 with an upwardly angled arm 126 spaced from the base. Arm 126 carries or forms a latch 128 having a proximal angled latching surface 130 joining a distal latching surface 132 disposed substantially transverse to the longitudinal axis of the handle and substantially parallel to the rail member rearward wall 108. Arm 126 has an extension 134 positioned distally of latch 128, and a releasing member or trigger 136 is juxtaposed with extension 134. The trigger 136 is pivotally mounted in housing 56 on a pin 138 secured to a wall or walls of the housing or structure supported in the housing, and the trigger is generally L-shaped with a leg 140 overlying extension 134 and a leg 142 extending transversely from leg 140 but at a slight angle toward the proximal end of the handle. A torsion spring (not shown) is coiled around pin 138 and fixed to trigger 136 to bias the trigger counterclockwise, looking at FIG. 2, such that leg 140 is biased toward extension 134.

In use, the handle 40 is typically supplied in the condition shown in FIG. 5 but without any medical instruments attached. In the condition shown, the tubular member 58 is in a retracted position where the rail member rearward wall 108 is adjacent the proximal end wall 62 of the housing, flange 88 abuts the forward wall 106 of rail member 104 due to the bias of bias member 112, and knob 78 is disposed at a proximal end of slot 74 due to the bias of retracting member 114.

Medical instruments can be attached to the handle 40 in a variety of ways, depending on the number and proximal configuration of the instruments. For example, in the case of a single medical instrument, such as needle 42, the proximal end of the instrument can be advanced proximally toward the tubular member 58 with the jaws 96 and 98 open as shown in FIG. 7, or closed as shown in FIG. 2, to frictionally couple the proximal end of the instrument with the cylindrical nub 84 at the distal end of the tubular member 58 so that the medical instrument and the tubular member will move together. If the jaws are opened to attach the medical instrument, the cylindrical nub 84 at the distal end of the tubular member will be exposed and, consequently, the proximal end of the instrument can be grasped and directly pushed onto the cylindrical nub to couple the instrument with the tubular member. If the proximal end of the medical instrument is about the same size as the bore, the jaws can be left closed and the medical instrument grasped distally of the proximal end so as to be advanced into the bore which will then serve as a guide centering the proximal end of the medical instrument with the nub to ease engagement.

In the case of two medical instruments being mounted, such as the needle 42 and catheter 44 shown, one is typically attached to the tubular member 58 in a manner to move with the tubular member and the other medical instrument is engaged by the jaws 96 and 98 in a manner to prevent movement. For needle 42 and catheter 44, the needle is telescopically received within the catheter and is held therein by frictional contact under normal handling conditions such that it will not easily fall off. Thus, the needle 42 can be attached to the tubular member of handle 40 in the manner previously described and the catheter 44 can be slid proximally over the needle until the base 54 of the catheter abuts the distal retaining surface 99 formed by the jaws 96 and 98 when the jaws are closed. Catheter 44 is then retained in place and prevented from moving further proximally by the jaws while the needle 42 is free to move within the catheter.

Alternatively, opposed surfaces of the jaws 96 and 98 can be configured to define a space, such as the annular recess shown in phantom at 161 in FIG. 2, for receiving and restraining the proximal end of the medical instrument to be held stationary when the jaws are closed; and, when opposed surfaces of the jaws are configured to engage the proximal end of a medical instrument, such as the base 54 of catheter 44, the jaws will normally be opened to permit positioning of the medical instrument between the jaws.

With one or more medical instruments attached, the handle 40 can be manually cocked or loaded to permit retraction of a medical instrument or left uncocked for use as a normal handle without retraction of a medical instrument. Operation of the retracting feature of the handle 40 will now be described with reference to use of a needle 42 and catheter 44 for penetrating an anatomical cavity. With needle 42 and catheter 44 attached to the handle 40 and prior to commencing penetration of the anatomical cavity wall W, knob 78 is grasped and manually moved distally to move the tubular member 58 and needle 42 distally against the bias of the retracting member 114 until the rearward wall 108 of rail member 104 rides over latch 128 by engaging the proximal latching surface 130 to move arm 126 toward base 122. At this time, the user can feel the rail member 104 lock into place in engagement with the distal latching surface 132 as arm 126 springs back and can also visually determine that the tubular member is locked in the extended position by noting the position of knob 78 within slot 74.

The handle 40 is now in the position illustrated in FIG. 2 with the tubular member 58 and needle 42 locked in the extended position by locking and releasing mechanism 118. In the extended position, the distal end of the catheter 44 is preferably spaced proximally of the beveled distal end 50 of the needle a distance x equal to the distance between the rail member forward wall 106 and the stop 77 so that the beveled distal end of the needle protrudes distally from the catheter in the extended position and lines up smoothly with the distal end of the catheter during penetration.

In order to penetrate the anatomical cavity wall W, handle 40 is gripped and needle 42 is pushed against the anatomical cavity wall. Referring now to FIG. 3, the force from tissue contact on the distal end 50 of the needle 42 causes the tubular member 58 to move proximally within the housing 56 as the distal end of the needle penetrates into the cavity wall. The force from tissue contact on the distal end of the needle also causes the operating member formed by flange 88 of the tubular member to move proximally until the flange abuts the stop 77 carried by rail member 104 which serves as an abutment limiting proximal movement of the tubular member relative to the rail member. The distal end of the catheter 44 is now aligned with the beveled tip 50 of the needle 42 to ease penetration. As the tubular member flange 88 moves proximally, the operating member formed thereby engages leg 142 to pivot trigger 136 clockwise, looking at FIG. 3, to allow the operating member to pass over the trigger. The clockwise pivotal movement of trigger 136 does not cause movement of the latch 128 since there is no engagement by either leg 140 or 142 with arm extension 134. Once the operating member passes by leg 142, the torsion spring biasing the leg returns trigger 136 to its normal position with leg 140 overlying arm extension 134. Since the rail member 104 remains stationary during penetration of the anatomical cavity wall, no force is required to overcome the bias of retracting member 114.

Once the distal end 50 of the needle 42 has passed through the anatomical cavity wall W, a reduction in the force from tissue contact on the distal end of the needle causes the tubular member 58 to move distally under the bias of bias member 112. As the tubular member moves distally, flange 88 engages leg 142 of trigger 136 causing the trigger to pivot counterclockwise looking at FIG. 4 and causing leg 140 to engage arm extension 134 moving the arm 126 toward base 122 against the resilient force of spring strip 120. The movement of arm 126 away from the longitudinal axis of the handle causes latch 128 to move out of engagement with the rail member rearward wall 108 thereby allowing retracting member 114 to move the tubular member 58 proximally to the retracted position where the rail member rearward wall 108 is disposed proximate the proximal end wall 62 of the housing and the distal end 50 of the needle 42 is retracted within the catheter 44 as illustrated in FIG. 5, thereby protecting tissue within the anatomical cavity from inadvertent contact with the distal end 50 of the needle. With the distal end of the catheter 44 located within the anatomical cavity, the handle 40 can be withdrawn from the catheter 44 as shown in FIG. 6 such that the needle 42 remains attached to the handle, leaving the catheter in place to form a portal in the anatomical cavity wall for passage of fluids and/or medical instruments. The needle 42 can then be removed from the handle 40 by separating the jaws 96 and 98, for example, and dislodging the base 46 of the needle 42 from the cylindrical nub 84 at the end of the tubular member 58 as shown in FIG. 7. Since jaws 96 and 98 can be opened to expose the base 46 of the needle 42, the user can grasp the needle near the proximal end for removal thereby avoiding body fluids and tissue which may be carried on or near the distal end 50 of the needle. The handle 40 can then be sterilized and prepared for use with new medical instruments in the manner previously described.

It will also be appreciated that if the first medical instrument is a penetrating member and the second a safety sheath, the penetrating member and safety sheath can be attached to the handle and passed through a separate portal sleeve so that the penetrating member is retracted into the safety sheath and both the safety sheath and the penetrating member can be removed together with the handle maintaining the tip of the penetrating member in a protected condition within the sheath and leaving the separate portal sleeve in place within the wall of the anatomical cavity to form a portal for the introduction of medical instruments and/or fluids.

A modification of the universal handle 40 of the present invention is shown in FIG. 8 at 146 wherein the upwardly angled arm 126 of locking spring 120 extends from a distal end of the base 122 and arm extension 134 terminates proximally in an upwardly turned portion 148 extending transversely toward the longitudinal axis of the housing to form a latching surface for engaging the rail member rearward wall 108 when the tubular member 58 is in the extended position shown. When the tubular member is in the retracted position, the upwardly turned portion 148 of arm extension 134 is disposed between the forward and rearward rail member walls, and the handle 146 can be locked in the extended or loaded position by advancing the knob 78 distally along the slot 74 formed in the top wall 66 of the housing causing the rail member forward wall 106 to engage trigger leg 142 such that trigger 136 is rotated counterclockwise looking at FIG. 8 to drive trigger leg 140 against arm extension 134. Depression of arm extension 134 toward base 122 causes the upwardly turned portion 148 of the spring to move away from the longitudinal axis of the housing allowing rail member rearward wall 108 to pass over the turned portion toward the extended position. Once cocked or loaded, use of the universal handle 146 is essentially the same as for handle 40 with the exception that counterclockwise rotation of trigger 136 for handle 146 causes disengagement of the upwardly turned portion 148 at the proximal end of arm extension 134.

FIG. 9 illustrates another modification of a universal handle according to the present invention wherein the locking spring of the modified handle 152 includes a flat base 154 secured to the proximal end wall 62 of the housing and a bend 156 joining the base with an arm 158 extending perpendicularly from the base in a distal direction. Arm 158 carries or forms a U-shaped latch 160 extending transversely toward the longitudinal axis of the housing for engaging the rail member rearward wall 108 when the tubular member 58 is in the extended position. A portion of the arm 158 extends distally beyond the latch 160 to be positioned beneath trigger leg 140 so that counterclockwise rotation of the trigger 136 causes the arm 158 to move away from the longitudinal axis of the handle. Also in FIG. 9, opposed inner faces or surfaces of jaws 96 and 98 are shown forming an annular recess 161 for receiving the base of a medical instrument, such as a catheter, to hold the medical instrument in a fixed position relative to the housing. It will be appreciated, however, that other gripping or clamping configurations can be defined depending on the shape of the proximal end of the medical instrument to be held and the force holding the jaws together.

Figure 10:
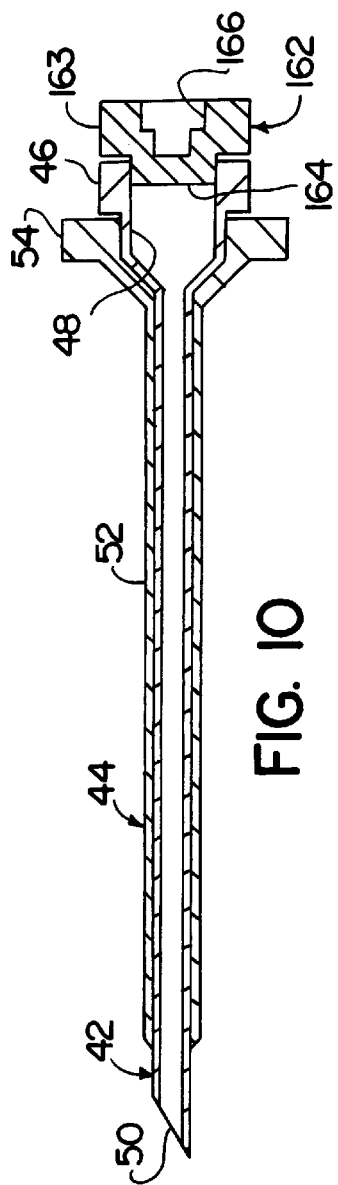
FIG. 10 is an enlarged, cross-sectional view of an adapter coupled with a conventional cannula and needle for use with the universal handle of the present invention.

In FIG. 10, an adapter 162 is shown engaging a proximal base portion 46 of a hollow needle 42 to prevent contamination of the handle by fluids entering the needle during penetration of an anatomical cavity wall and to convert the proximal end of the needle for use with the universal handle of the present invention. The adapter 162 includes a cylindrical body 163 having an adapter protrusion 164 at a distal end engagable with the proximal end of a medical instrument, such as the base portion 46 of the hollow needle 42, and an adapter socket or recess 166 at a proximal end engagable with the distal end 84 of a mounting member, such as tubular member 58. In use, an adapter 162 is selected having a distal protrusion 164 configured to mount the proximal end of a medical instrument to be coupled with a universal handle according to the present invention. The adapter 162 is inserted into the proximal end of the medical instrument and is held in place by frictional engagement. The medical instrument will then move with the adapter so that when the adapter is mounted on the distal end of the mounting member, movement of the mounting member will be imparted to the medical instrument. It will be appreciated, therefore, that use of an adapter permits medical instruments having various proximal end configurations to be mounted on the universal handle of the present invention. Accordingly, the distal end of the adapter can have any configuration suitable for engaging the proximal end of a medical instrument, including threaded or unthreaded protrusions or sockets, Luer locks or detent structures, for example; and the proximal end of the adapter can have any configuration suitable for engaging the distal end of a mounting member, including threaded or unthreaded protrusions or sockets, Luer locks or detent structures, for example.

Figure 11:
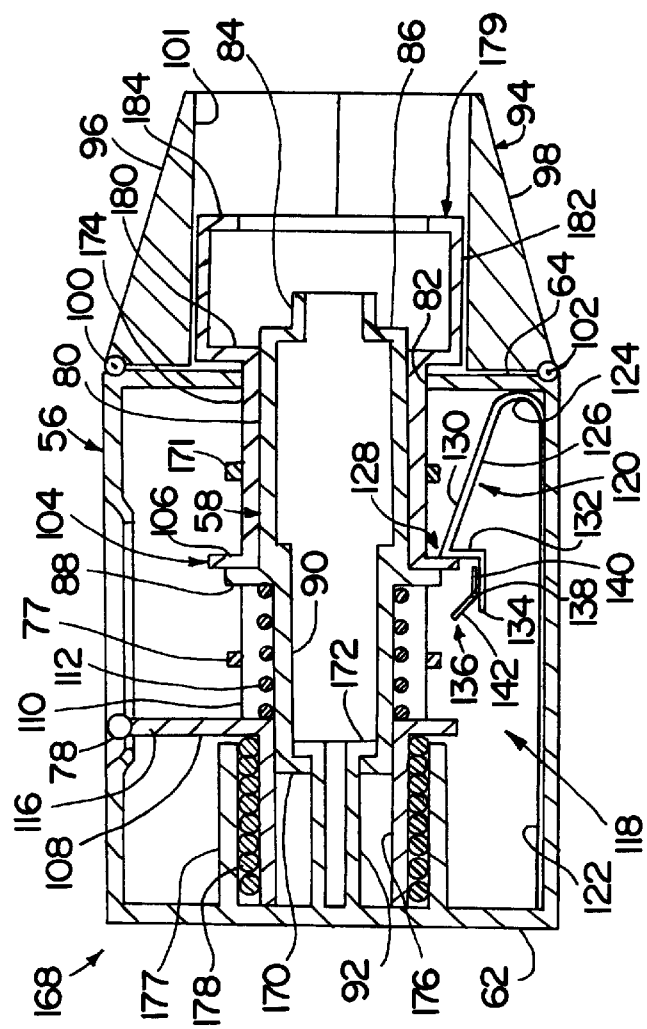
FIG. 11 is a side view, partly in section, of a further modification of the universal handle according to the present invention.

A further modification of the universal handle according to the present invention is illustrated in FIG. 11 wherein the modified handle 168 is configured to move a first medical instrument, such as a cannula, distally from a retracted position exposing the distal end of a second medical instrument, such as a penetrating member, to an extended protruding position shielding the distal end of the second medical instrument.

Housing 56 and tubular member 58 for handle 168 are similar to those previously described with the exception of an annular rim 170 formed on an inside surface of the second cylindrical portion 90 of the tubular member 58 and a stop member 171 configured to engage the rail member 104. Guide tube 92 extends through the annular rim 170 and terminates distally at a transverse flange 172 which serves as a stop or abutment for rim 170 limiting distal movement of the tubular member relative to the housing. Stop member 171 extends from a wall or walls of the housing and is distally spaced from the rail member forward wall 106 to limit distal movement of the rail member within the housing. As shown, stop member 171 includes a wall having an opening formed therethrough for passage of a first cylindrical portion 174 of the rail member. Alternatively, stop member 171 could include a pair of posts, for example, extending from lateral side walls of the housing on opposite sides of the rail member and positioned between the rail member forward wall 106 and proximal end wall 64 of the housing.

With reference to FIGS. 11 and 12, it can be seen that rail member 104 for handle 168 includes first cylindrical portion 174 extending distally from the rail member forward wall 106 through the opening 82 in the distal end wall 64 of the housing, and a second cylindrical portion 176 extending proximally from the rail member rearward wall 108 to abut the proximal end wall 62 of the housing when the rail member is in the loaded, retracted position shown in FIG. 11. First and second cylindrical portions 80 and 90 of the tubular mounting member 58 are telescopically fitted within the first and second cylindrical portions 174 and 176 of the rail member, respectively, for sliding movement therein. Flange 88 of the tubular member is disposed between the forward and rearward walls 106 and 108 of the rail member distally of stop 77 attached to the rail member sidewall 110.

An extending member 178 is disposed around the second cylindrical portion 176 of the rail member within a cylindrical guide wall 177 extending from the proximal end wall 62 of the housing and is held in compression between the proximal end wall 62 of the housing and the rail member rearward wall 108 to bias the rail member 104 in a distal direction relative to the housing. The first cylindrical portion 174 of the rail member 104 carries a receptacle, socket or collar 179 at a distal end for receiving the proximal end of a medical instrument so that the rail member can also serve as a mounting member. The receptacle 179 is disposed externally of the housing and includes an annular flange 180 extending part way around the distal end of the first cylindrical portion 174, a semicylindrical wall 182 extending distally from a peripheral edge of the flange 180 and an inwardly extending lip 184 formed along a distal edge of the wall. The receptacle 179 is movable within bore 101 formed between jaws 96 and 98 but is prevented from moving beyond the jaws by engagement of the stop member 171 with the forward wall 106 of the rail member. Thus, any instrument held in the receptacle is prevented from becoming laterally dislodged from the collar during movement of the rail member relative to the housing. It will also be appreciated that lip 184 can be configured to engage the proximal end of an instrument to prevent distal movement of the instrument from the receptacle.

Stop 77 for handle 168 is mounted on the rail member side wall 110 for limiting proximal movement of the tubular member flange 88 relative to the rail member 104 and, thus, any medical instrument carried at the distal end 84 of the tubular member. A bias member 112 is disposed around the tubular member 58 and is held in compression between the rail member rearward wall 108 and the tubular member flange 88 to bias the tubular member flange distally toward the rail member forward wall 106.

Locking and releasing mechanism 118 for handle 168 is similar to that shown in FIG. 2 but with upwardly angled arm 126 extending from the distal end 186 of the base 122 to form an angled distal latching surface 130 and a proximal latching surface 132 parallel to rail member forward wall 106. Arm extension 134 extends horizontally from a bottom end of the proximal latching surface 132 and is juxtaposed with the horizontal leg 140 of trigger 136.

Figure 14:
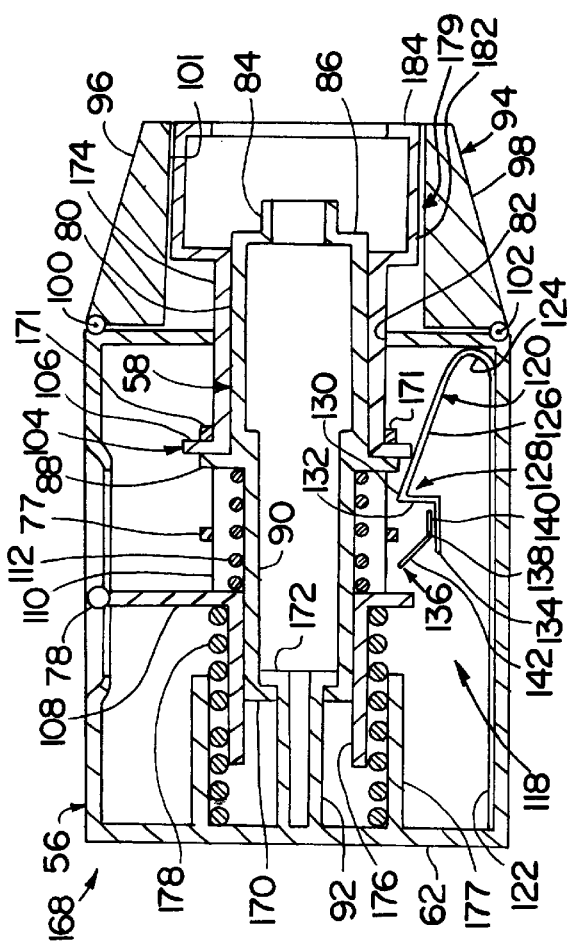

In use, handle 168 is normally supplied in the condition shown in FIG. 14 with the rail member 104 in the unloaded, extended position. In the extended position shown, rail member forward wall 106 abuts stop 171 due to the bias of extending member 178 and tubular member 58 is in a rest position where flange 88 abuts rail member forward wall 106 due to the bias of bias member 112. A first medical instrument, such as catheter 44, is fitted within the semicylindrical receptacle 179 at the distal end of the rail member 104 with the wedge-shaped jaws 96 and 98 of the housing collar 94 pivoted apart to be in the open condition. The base of a second medical instrument, such as a needle 42 disposed within the catheter 44, is then seated on the cylindrical nub 84 at the distal end of the tubular mounting member 58 and the jaws closed. The handle 168 is cocked or loaded by drawing the knob 78 proximally along slot 74 to move the rail member 104 proximally against the bias of extending member 178 until the rail member forward wall 106 is engaged by the proximal latching surface 132 of the latch spring as shown in FIG. 11. If a catheter is being held by the handle, the distal end of the catheter is now preferably proximally spaced from the distal end of the needle disposed within the catheter such that the sharp distal end of the needle is exposed.

When the second medical instrument carried by the tubular member is advanced against a surface, for example to penetrate an anatomical cavity wall, the counterforce on the instrument will cause the tubular member 58 to move proximally within the housing against the distal bias of bias member 112. At the same time, the operating member formed by flange 88 of the tubular member engages leg 142 of trigger 136 to pivot the trigger counterclockwise, looking at FIG. 13, thereby allowing the operating member to move past the trigger leg 142. The counterclockwise pivotal movement of trigger 136 does not cause movement of the latch 128 since there is no engagement by either leg 140 or 142 with arm extension 134. Once the operating member passes by leg 142, a torsion spring returns trigger 136 to its normal position with leg 140 adjacent arm extension 134 as shown in FIG. 13. Accordingly, during advancement of the second medical instrument against a surface, no force is required to overcome the bias of extending member 178.

Once the distal end of the second medical instrument has passed through the surface, a reduction in force from contact with the surface will cause the second medical instrument to move distally under the bias of bias member 112. As the second medical instrument moves distally, flange 88 of the tubular member engages leg 142 of trigger 136 causing the trigger to pivot clockwise looking at FIG. 13 and causing leg 140 to engage arm extension 134 moving arm 126 toward base 122 against the force of spring strip 120. The movement of arm 126 away from the longitudinal axis of the handle causes latch 128 to move out of engagement with the rail member forward wall 106 thereby allowing extending member 178 to move the rail member distally to the extended protruding position illustrated in FIG. 14. If the first medical instrument is a cannula and the second medical instrument is a penetrating member, movement of the rail member distally from the retracted position shown in FIG. 11 to the extended position shown in FIG. 14 will preferably cause the cannula to protrude beyond the distal end of the penetrating member to protect tissue within an anatomical cavity from inadvertent contact with the distal end of the penetrating member. With the cannula placed in the anatomical cavity wall, jaws 96 and 98 can be pivoted away from one another on pins or hinges 100 and 102 releasing the proximal end of the cannula from the semicylindrical receptacle 179 so that the handle can be withdrawn with the penetrating member from the cavity leaving the cannula in place to serve as a portal through the anatomical cavity wall. It will also be appreciated that if the second medical instrument is a penetrating member and the first a safety member such as a safety shield or probe, the penetrating member and safety member can be attached to the handle and passed through a separate portal sleeve so that the safety shield or probe will be extended beyond the distal tip of the penetrating member upon penetrating into the anatomical cavity and both the safety member and the penetrating member can be removed together with the handle so that the tip of the penetrating member will be maintained in a protected position within the safety member while the separate portal sleeve will be left in place to form a portal within the wall of the cavity.

Figure 15:
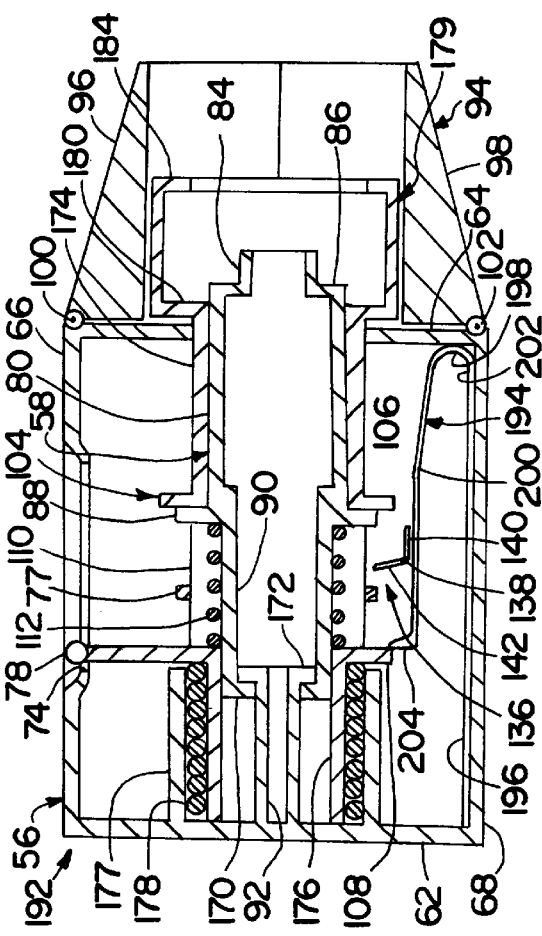
FIG. 15 is a side view, partly in section, of still another modification of the universal handle according to the present invention.

The modified handle 192 shown in FIG. 15 is similar to handle 168 shown in FIGS. 11–14 but with a different locking spring. Locking spring 194 for handle 192 includes a flat base 196 secured to the bottom wall 68 of the housing 56 and a U-shaped bend 198 joining the distal end of an arm 200 with a distal end 202 of the base. Arm 200 extends substantially parallel to a longitudinal axis of the handle and terminates proximally at an upwardly angled portion 204 forming a latch for engaging the distal face of the rail member rearward wall 108 when the rail member 104 is in the retracted position shown. Trigger 136 is positioned in the housing 56 with leg 140 overlying the arm 200 and leg 142 positioned proximally of the operating member formed by the tubular member flange 88 so that projection of the rail member 104 to the extended position is triggered by distally-biased movement of the tubular member 58. From the extended position, the handle 192 is cocked or loaded by advancing knob 78 proximally along slot 74 formed in the housing top wall 66 to cause rail member rearward wall 108 to slide over the upwardly angled portion 204 depressing the arm 200 away from the longitudinal axis of the handle and towards the base 196. When rail member rearward wall 108 passes over the angled portion 204, the arm 200 springs back toward the longitudinal axis, latching the rail member rearward wall in the retracted position shown in FIG. 15.

FIG. 16 illustrates another modification of the handle shown in FIGS. 11–14 wherein the locking spring of the modified handle 206 includes a flat base 208 secured to the distal end wall 64 of the housing and a bend 210 joining the base with an arm 212 extending perpendicularly from the base in a proximal direction. Arm 212 is doubly folded intermediate its length to form a U-shaped latch 214, like latch 160 for handle 152, for engaging the distal face of the rail member forward wall 106 when the rail member is in the retracted position. Also shown is a tapered control button 216, similar to that shown and described in applicant's copending patent application Ser. No. 08/083,220, which extends transversely or into the plane of the drawing between lateral sidewalls 70 and 72. Control button 216 is located proximate arm 212 of the locking spring within a curved portion 213 of the arm and is tapered along its length to form a wedge which, when depressed, moves the arm away from the longitudinal axis of the housing to disengage the latch. Operation of the control button 216 to disengage the latch allows rail member forward wall 106 to pass over latch 214 for manual loading of the handle and can also be used to unload the handle so that, for example, the handle can be used merely to hold a medical instrument without providing a retracting or extending function.

A further modification of the handle according to the present invention is shown in FIG. 17 wherein the modified handle 218 is similar to handle 168 illustrated in FIGS. 11–14 but with the bias member 112 disposed around the guide tube 92 and held in compression between the proximal end wall 62 of the housing and the proximal end or rim 170 of the tubular member 58. The location of the bias member 112 for handle 218 is particularly advantageous in that when the rail member 104 and tubular member 58 are to be stored for extended periods of time, bias springs 112 and 178 can be maintained in extended positions such that the resilience of the springs remains substantially unaffected over time. Moreover, in the handle of FIG. 17, rail member forward wall 106 extends toward housing upper wall 66 with a post 116 extending from the rail member forward wall 106 through a slot 74 formed proximate the distal end of the housing and terminating at a knob 78 disposed within an elongate recess 76.

The modified handle 220 shown in FIG. 18 differs from handle 168 illustrated in FIGS. 11–14 primarily in the distal configuration of the rail member 104 and the position of stops 77. Rail member 104 for handle 220 is similar to that shown in FIG. 11 but with a cylindrical socket 222 and an annular ridge or seat 224 formed at the bottom or proximal end of the cylindrical socket for receiving and frictionally engaging the base 54 of a catheter 44 or other medical instrument. As a result, jaws are not needed to retain and guide a medical instrument such as a catheter 44 held within the socket 222 as the medical instrument is advanced to an extended position protruding beyond the distal end of a needle 42 or other medical instrument. Annular ridge 224 is configured to allow passage of a needle base 46, for example, so that the base at the proximal end of the needle can mate with the distal end of tubular member 58, which forms a cylindrical recess 226 for receiving and frictionally engaging the exterior surface of the needle base. A wall 228 at the bottom of recess 226 forms a stop limiting proximal movement of the needle base relative to the tubular member. Stops 77 for handle 220 extend from a wall or walls of the rail member through slots 229 formed in the tubular member 58 to limit movement of the tubular member relative to the rail member. The length of slots 229 is preferably equal to the distance between the catheter distal end and needle distal end when a catheter is mounted to be retracted so that the distal ends of the catheter and needle will line up in response to the force from tissue contact when the needle is pressed against anatomical tissue to be penetrated. Operation of the handle 220 is essentially the same as for handle 168 with the exception that medical instruments such as the needle 42 and catheter 44 are mounted without the use of jaws.

FIG. 19 illustrates a modification of the handle shown in FIG. 18 wherein the modified handle 232 is configured to mount a penetrating member in the form of a trocar 234 and a cannula in the form of a portal sleeve 236. Trocar 234 includes a cylindrical obturating body 238 with an externally threaded proximal end 240 and facets 242 at a distal end conjoining to form a tissue penetrating tip 244. Portal sleeve 236 is telescopically fitted over trocar 234 and includes a distal end 246 and an externally threaded proximal end 248. Cylindrical socket 222 for handle 232 is internally threaded at 250 to receive the proximal end 248 of portal sleeve 236. Similarly, the cylindrical recess 226 at the distal end of tubular member 58 is internally threaded at 252 to threadedly receive the proximal end 240 of trocar 234. Use of handle 232 is essentially the same as for handle 168 with the exception that the housing 56 or portal sleeve 236 must be rotated or unscrewed after penetration to release the portal sleeve from the handle so that the trocar 234 can be withdrawn from the anatomical cavity along with the handle 232 leaving the portal sleeve in place to serve as a portal for introducing medical instruments into the anatomical cavity. Alternatively, trocar 234 and sleeve 236 can be inserted through a larger cannula or portal sleeve so that sleeve 236 functions as a safety shield and is thereafter withdrawn from the larger cannula along with the trocar.

Figure 20:
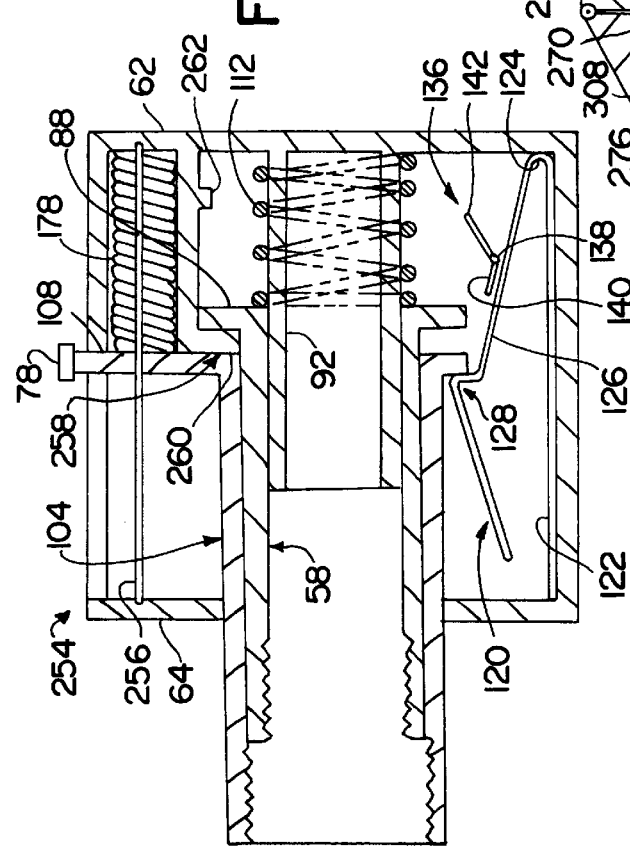
FIG. 20 is a side view, partly in section, of another modified universal handle according to the present invention.

FIG. 20 shows another modification of the handle according to the present invention which performs a similar protruding or extending function as that described in connection with FIGS. 11–19. The major difference between the handle 254 shown in FIG. 20 and the other handles resides in the location of the extending member 178 and the bias member 112. In FIG. 20, the rail member 104 has only a rearward wall or flange 108 which engages latch 128 of the locking spring 120 due to the force of the extending member 178 acting on the rearward wall 108 of the rail member. The extending member 178 is mounted in compression between the proximal end wall 62 of the housing and the rearward wall 108 of the rail member 104 and is disposed around a control rod 256 connected between proximal and distal end walls 62 and 64 of the housing.

Referring still to FIG. 20, the bias member 112 is disposed around guide tube 92 and is held in compression between the proximal end wall 62 and the annular flange portion 88 of the tubular mounting member 58. Guide tube 92 is received within the tubular member 58 and bias member 112 applies a distal biasing force to the tubular member 58 which resists movement of the tubular member toward the proximal end wall. Moreover, in the handle of FIG. 20, there is a projection 258 having an L-shaped cross-section that is integral with and extends from the proximal end wall 62. The L-shaped projection 258 limits distal movement of the tubular member 58 within the housing. That is, the movement of the tubular member 58 due to the biasing force of bias member 112 is limited by the engagement of the annular flange portion 88 of the tubular member 58 with a retaining shoulder portion 260 of the L-shaped projection 258. The function of the L-shaped projection 258 is to prevent the tubular member 258 from extending beyond the retaining shoulder portion 260 so that the distal end of the tubular member will not extend too far toward the distal end of the housing. An annular protrusion 262 extends inwardly from the L-shaped projection 258 and serves as a stop to limit the movement of the annular flange portion 88 in the proximal direction.

The handle shown in FIG. 20 operates in a manner similar to those previously described in that, when an external force is applied to the tubular member 58, as in the case of a resistant force caused by tissue contact during penetration, the tubular member 58 is moved proximally against the bias of bias member 112 and passes over leg 142 of trigger 136 without disengaging the rail member rearward wall 108 from the latch 128 formed by spring 120. However, upon penetration, the force from tissue contact is reduced to a level below the biasing force of the bias member and the tubular member 58 will move in a distal direction into contact with leg 142 forcing the spring 120 downward until the rail member rearward wall 108 is not retainingly engaged by the latch 128 formed by spring 120. When this occurs, the biasing force of the extending member 178 will act on the rail member rearward wall 108 to protrude or extend the rail member 104 toward the distal end wall 64 of the housing. Thus, any instrument mounted by the rail member will be moved to an extended position where the distal end of the instrument protrudes beyond the distal end of another instrument mounted by the tubular member, for example, to serve as a safety shield.

Figure 21:
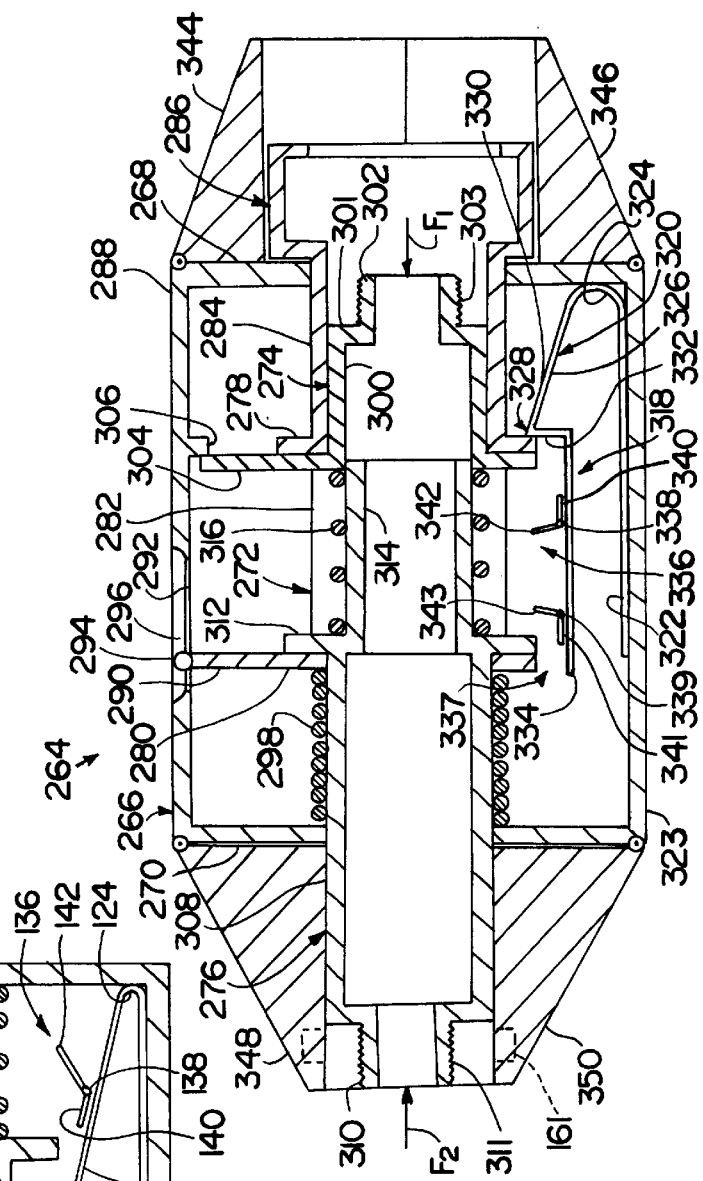
FIG. 21 is a side view of another modification of a universal handle according to the present invention.

FIG. 21 illustrates still another modification of the universal handle according to the present invention wherein a first end of the modified handle 264 is configured to move a medical instrument, such as a cannula, distally from a retracted position to an extended position and a second end of the modified handle is configured to move a medical instrument, such as a penetrating member, proximally from an extended position to a retracted position. The modified handle 264 includes a housing 266 having opposed first and second end walls 268 and 270, a rail member 272 movable within the housing between the end walls, first and second tubular mounting members 274 and 276 mounted by the rail member for sliding movement, and a combination retracting and protruding mechanism for locking the rail member in a first position proximate one of the end walls and for releasing the rail member to be moved toward the other end wall in response to a reduction in force acting on either the first or second tubular members.

Rail member 272 is similar to that shown in FIG. 12 at 104 but without a second cylindrical portion. More specifically, the rail member 272 for handle 264 includes a first flange or wall 278 disposed transverse or perpendicular to a longitudinal axis of the housing, a second flange or wall 280 disposed between the first flange 278 and the second end wall 270 in configuration parallel to the first flange 278, a side wall 282 transversely joining the first and second flanges of the rail member, a cylindrical portion 284 extending from the first rail member flange and through an opening in the first end wall 268 of the housing, and a semicylindrical receptacle 286, similar to receptacle 179, carried at a distal end of the cylindrical portion 284 externally of the housing for receiving the proximal end of a medical instrument. The second rail member flange 280 extends toward the top wall 288 of housing 266 and a post 290 extends from the second rail member flange 280 through a slot 292 in the housing top wall 288 to terminate at a knob 294 positioned in an elongate, trough-like recess 296 formed in the housing top wall. Slot 292 and recess 296 extend longitudinally in parallel with the longitudinal axis of the handle 264. A bias member 298 is mounted between the second rail member flange 280 and the second end wall 270 of the housing to bias the rail member 272 toward the first end wall 268. The bias member 298 can include a helical coil spring mounted in compression between the second rail member flange 280 and the second end wall 270 of the housing as shown, or the bias member can include any other type of spring or other bias device as discussed above.

The first tubular mounting member 274 includes a hollow cylindrical body 300 telescopically fitted within the cylindrical portion 284 of rail member 272 for sliding movement therein. The cylindrical body 300 extends from a transverse flange 304 disposed between the rail member flanges 278 and 280 and terminates within the cylindrical portion 284 at an annular step or shoulder 301 joining the cylindrical body with a diametrically smaller cylindrical nub 302 having external threads 303. A stop 306 extends perpendicularly from the top wall of the housing in the direction of the first tubular member to serve as an abutment member for engaging the flange 304 of the first tubular member to limit movement of the first tubular member relative to the housing in the direction of the first end wall 268.

The second tubular mounting member 276 includes a first cylindrical portion 308 slidably disposed within aligned openings formed in the second rail member flange 280 and the second end wall 270 of the housing, a cylindrical nub 310 with external threads 311 carried at an end of the first cylindrical portion passing through the opening in the second end wall 270, a round flange 312 disposed at the opposite end of the first cylindrical portion between first and second rail member flanges 278 and 280, and a second cylindrical portion 314 extending from the flange 312 in the direction of the first end wall 268 to be telescopically received within the hollow body 300 of the first tubular member 274 for sliding movement therein.

A second bias member 316 is connected between flange 304 of the first tubular member and flange 312 of the second tubular member to bias the tubular members apart and into rest positions where they abut first and second rail member flanges 278 and 280, respectively. As shown, bias member 316 includes a helical coil spring disposed around the second cylindrical portion 314 of the second tubular member and mounted in compression between flanges 304 and 312. However, bias member 316 can include various other types of springs as well as other types of bias devices including compression springs, tension springs, torsion springs, pan springs, leaf springs, rubber, plastic or magnets, for example.

Locking and releasing mechanism 318 for locking the rail member in a loaded, cocked position proximate the second end wall of the housing and for releasing the rail member to allow the bias member to move the rail member toward the first end wall of the housing includes a latch or locking spring 320, made of a strip of resilient material, formed to have a substantially flat base 322 secured to the bottom wall 323 of the housing and a bend 324 joining the base 322 with an upwardly angled arm 326 spaced from the base. Arm 326 carries or forms a latch 328 having an angled latching surface 330 joining a transverse latching surface 332 disposed substantially perpendicular to the longitudinal axis of the handle and substantially parallel to the first rail member flange. Arm 326 has a horizontal extension 334 extending from a bottom of the transverse latching surface, and a pair of spaced releasing members or triggers 336 and 337 juxtaposed with extension 334. Trigger 336 is pivotally mounted in the housing on a pin 338 secured to a wall or walls of the housing or structure supported in the housing and is generally L-shaped with a leg 340 overlying extension 334 and a leg 342 extending transversely from leg 340 but at a slight angle toward the second end wall of the handle. A torsion spring (not shown) is coiled around pin 338 and fixed to trigger 336 to bias the trigger clockwise, looking at FIG. 21, such that leg 340 is biased toward extension 334. The trigger 337 is pivotally mounted in the housing on a pin 339 secured to a wall or walls of the housing or structure supported in the housing, and is also generally L-shaped with a leg 341 overlying extension 334 and a leg 343 extending transversely from leg 340 but at a slight angle toward the first end wall of the housing. A torsion spring (not shown) is coiled around pin 339 and fixed to trigger 337 to bias the trigger counterclockwise, looking at FIG. 21, such that leg 341 is biased toward extension 334.

Jaws 344 and 346 proximate the first end wall 268 of the housing are the same as the jaws shown in FIG. 11, and jaws 348 and 350 proximate the second end wall 270 are the same as the jaws shown in FIG. 2. It will be appreciated, however, that opposed surfaces of jaws 348 and 350 can also be configured to define a space, such as the annular recess shown in phantom at 161 in FIG. 21, for receiving the proximal end of a medical instrument to prevent movement of the instrument relative to the housing.

Figure 23:
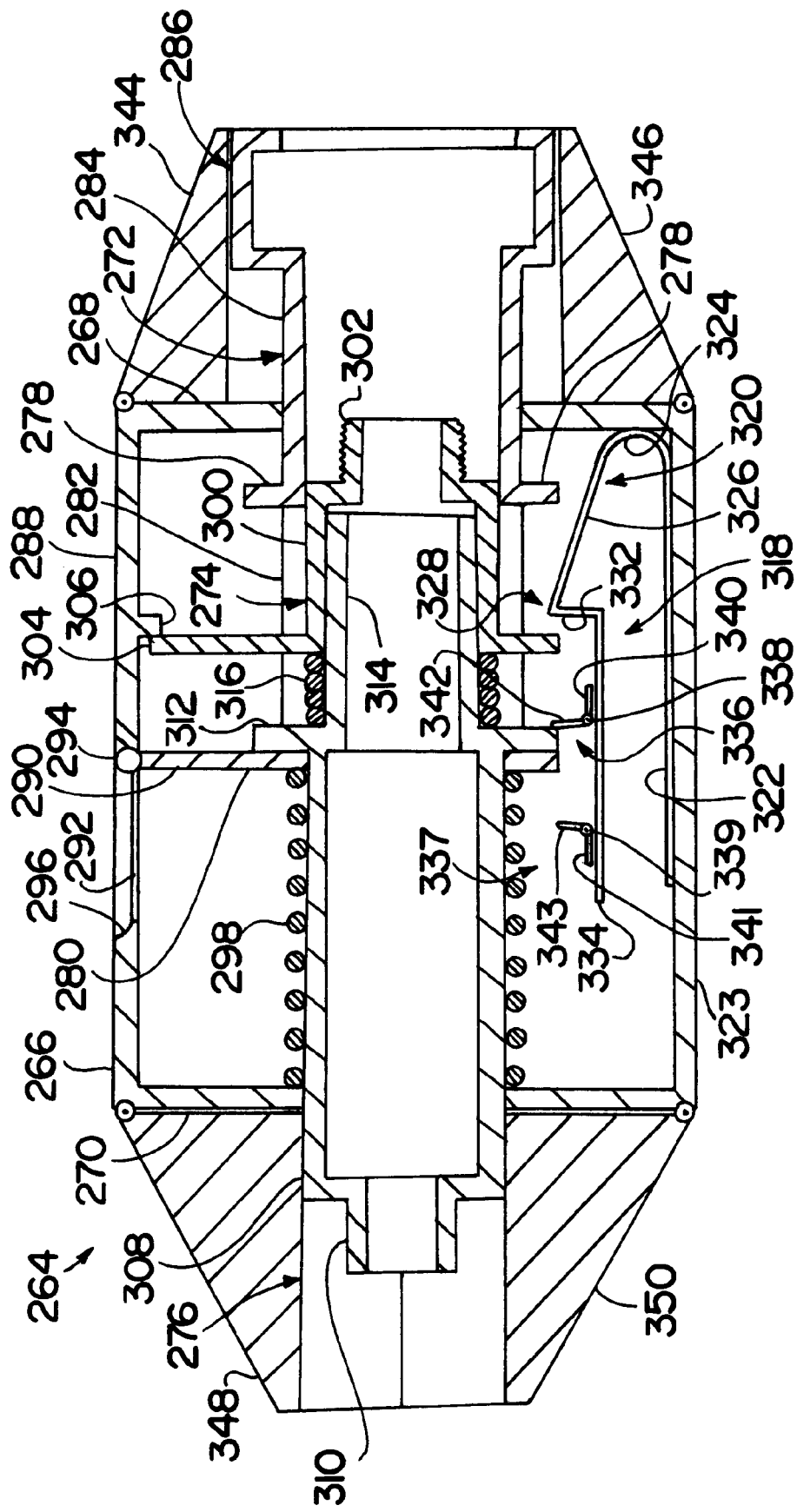

In use, the modified universal handle 264 is preferably supplied in the unloaded condition shown in FIG. 23 wherein the bias member 298 is in an extended condition, the first tubular member flange 304 abuts stop member 306 and the knob 294 is disposed at the end of slot 292 closest the first end wall of the housing. Prior to cocking the handle, medical instruments such as penetrating members and cannulas are mounted on either side of the handle depending on the desirability of having one instrument retract or protrude relative to the other instrument or the housing. For purposes of clarity, operation of the handle 264 will be explained without reference to any particular type of medical instruments.

Figure 22:
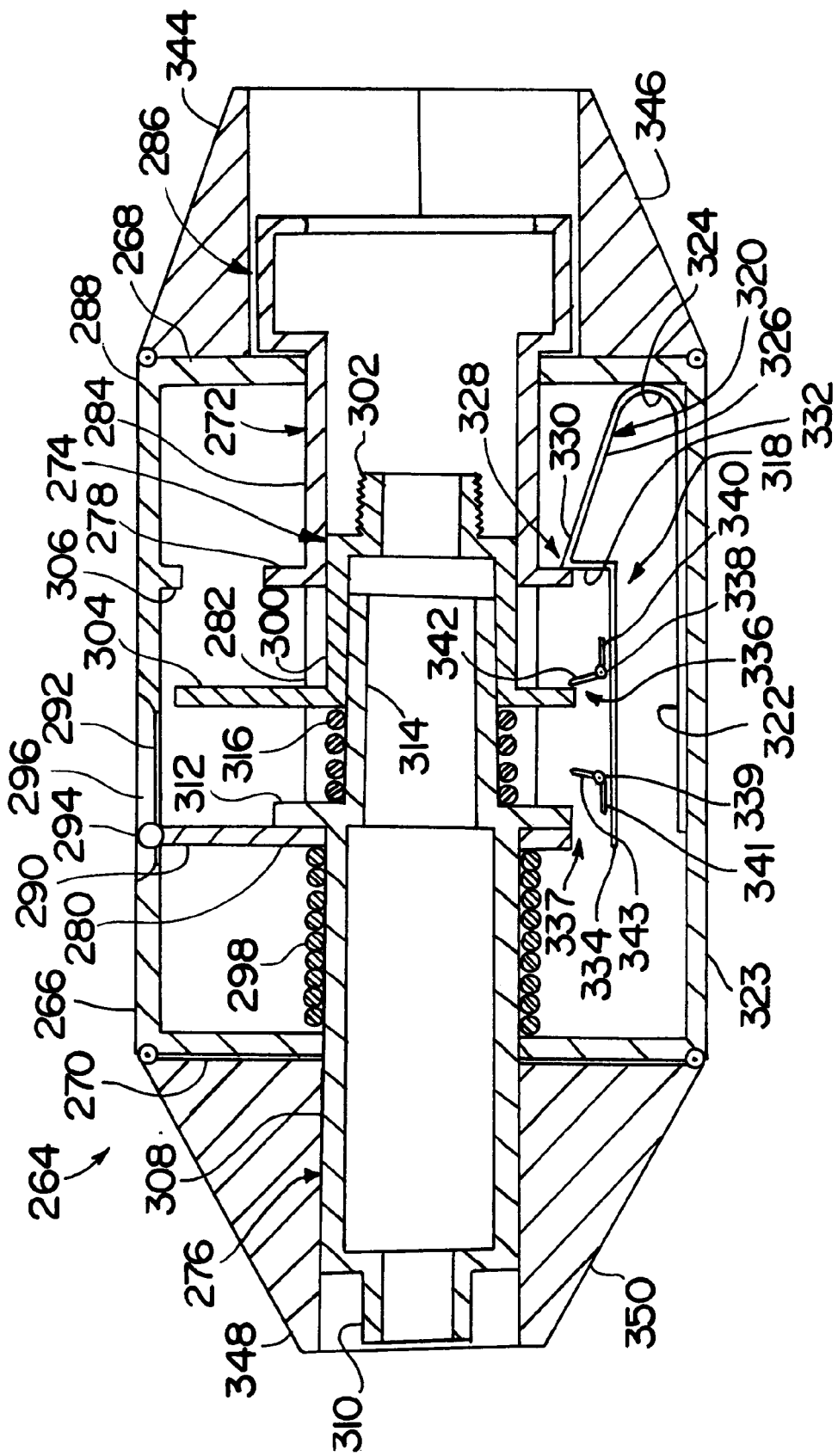
FIGS. 22–25 are side views, partly in section, illustrating operation of the universal handle shown in FIG. 21.

Referring still to FIG. 23, the handle 264 is cocked or loaded by sliding knob 294 along slot 292 towards the opposite end of the slot until the first rail member flange 278 slides over the latch 328 and is engaged by the transverse latching surface 332. The handle 264 is now in the cocked or loaded condition shown in FIG. 21. When a first initial external force $F_1$ is exerted on the first tubular member 274 in the loaded condition, causing it to move against the biasing force of the second bias member 316, the operating member formed by the flange 304 of the first tubular member 274 passes over transverse leg 342 of the trigger 336 causing the trigger to rotate counterclockwise looking at FIG. 21 without releasing the engagement of the latch 328 with the first flange 278 of rail member 272. However, when the force being applied to the first tubular member is reduced to a level below the biasing force of the second bias member 316, the first tubular member 274 moves back toward the trigger mechanism 336 as shown in FIG. 22 and engages the transverse leg 342 of the trigger mechanism causing the trigger 336 to rotate clockwise looking at FIG. 22, thereby forcing arm extension 334 of locking spring 320 downward and releasing the first flange 278 of the rail member 272 from the latch 328 formed by the upwardly angled arm 326. The biasing force of the first bias member 298 then moves the rail member 272 in the direction opposite that of the first initial external force, so that the collar 286 and any instrument held in the collar are moved away from the housing toward the extended position shown in FIG. 23. Accordingly, if the first tubular member 274 is adapted to receive the proximal end of a needle, for example, and the rail member 272 is configured to receive the proximal end of a catheter surrounding the needle (for example as shown in FIG. 2), the outward movement of the rail member 272 can be designed to travel to a point whereby the distal end of the catheter will cover the sharp tip of the needle.

It will also be appreciated that if the first tubular member is adapted to couple with a penetrating member and the rail member a safety member such as a safety shield or probe, the penetrating member and safety member can be attached to the handle and passed through a separate portal sleeve so that the safety shield or probe will be extended beyond the distal tip of the penetrating member upon penetrating into the anatomical cavity and both the safety member and the penetrating member can be removed together with the handle so that the tip of the penetrating member will be maintained in a protected position within the safety member while the separate portal sleeve will be left in place to form a portal within the wall of the cavity.

Figure 24:
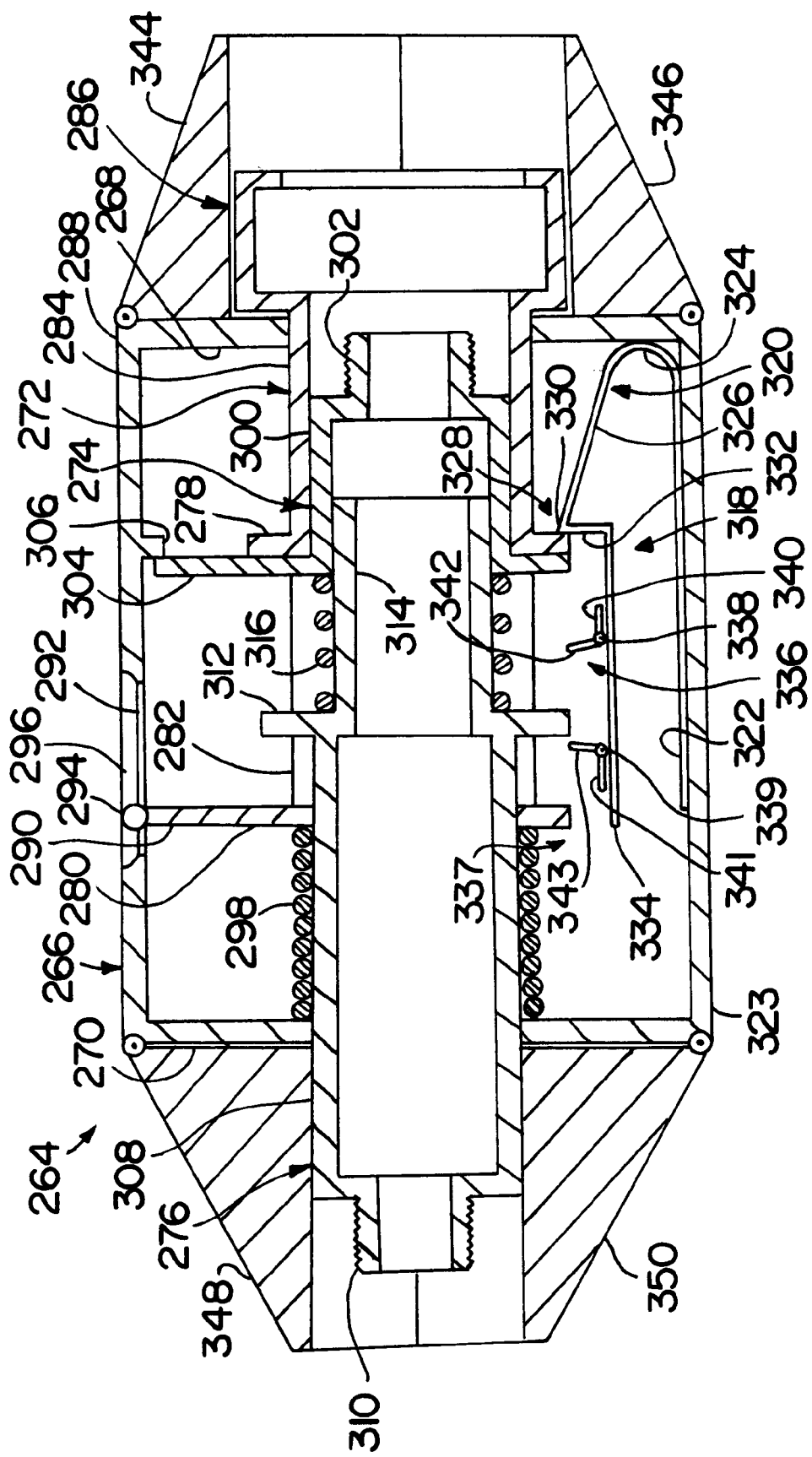
Figure 25:
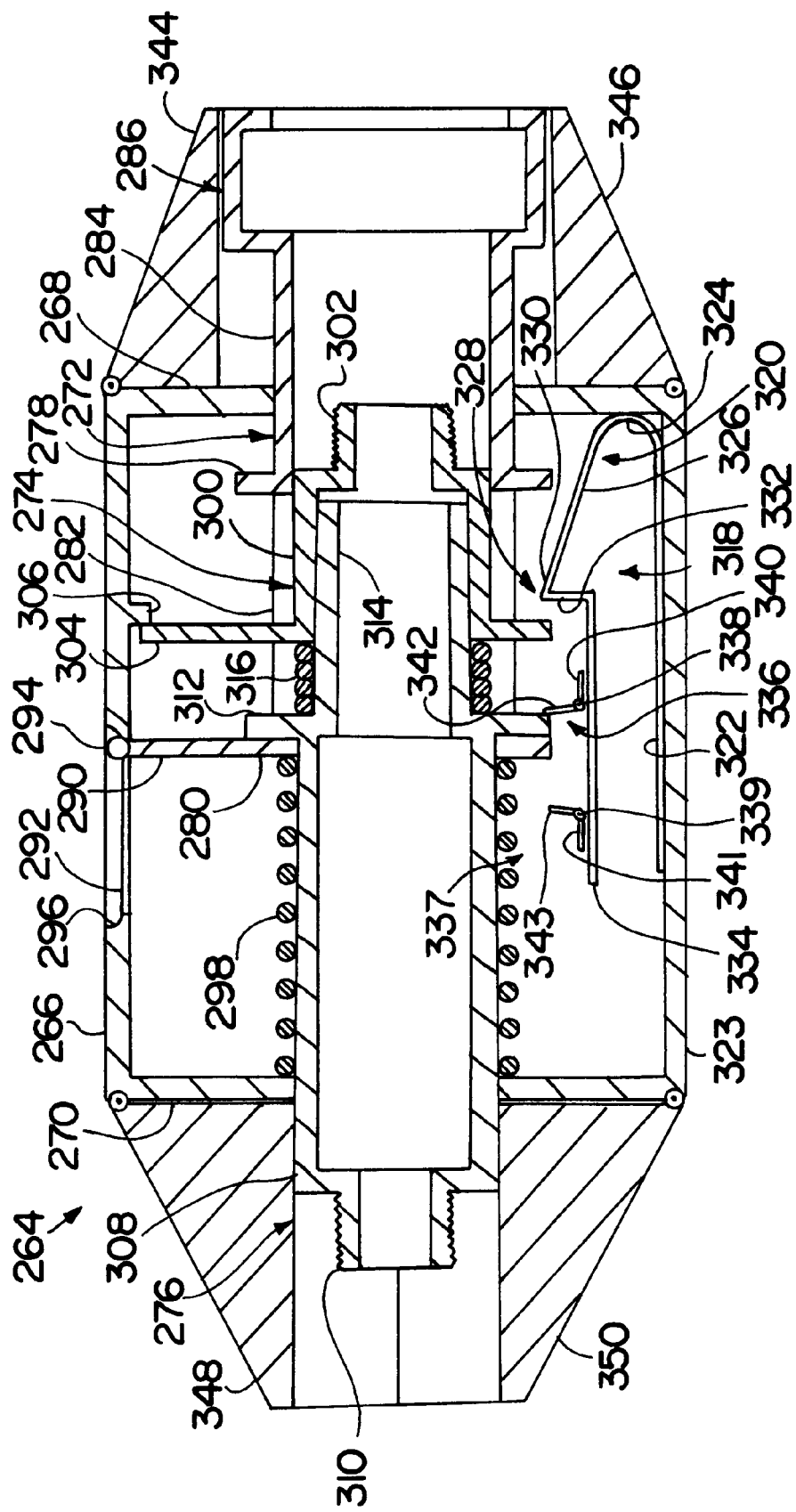

On the other hand, when a second initial external force $F_2$ is applied to the second tubular member 276 of a cocked handle, as shown in FIG. 21, the second tubular member is moved against the biasing force of the second bias member 316, and the operating member formed by flange 312 of the second tubular member 276 passes over the transverse leg 343 of the second trigger 337 causing the trigger to rotate clockwise looking at FIG. 21 without disengaging the latch 328 from the first flange portion 278 of the rail member 272. However, when the applied force is reduced to a level below the biasing force of the second bias member 316, the second bias member will move the second tubular member 276 in the direction opposite the initial external force, toward the second end wall 270 of the housing, whereby the annular flange 312 of the second tubular member contacts the transverse leg 343 of the second trigger mechanism 337 as shown in FIG. 24, rotating the trigger counterclockwise looking at FIG. 24, and thereby forcing the arm extension 334 of locking spring 320 in a downward direction away from the longitudinal axis of the handle which releases the engagement of the first flange portion 278 of rail member 272 from the shoulder or latch 328 of the spring arm 320. When this occurs, bias member 298 moves the rail member 272 in the same direction as the second initial external force to the extended position proximate the first end wall 268 of the housing 266. Movement of the rail member 272 toward the first end wall 268 causes rail member flange 280 to engage the flange 312 of the second tubular member 276, carrying the second tubular member in the direction of the first end wall to a retracted position relative to the housing as shown in FIG. 25. Accordingly, if the second tubular member 276 is adapted to receive the proximal end of a needle and the jaws 348 and 350 are adapted to receive or support a proximal end of a catheter surrounding the needle (for example as shown in FIG. 2), the inward movement of the second tubular member 276 can be designed to travel to a point whereby the distal end of the needle will be disposed proximally of the distal end of the catheter so as to be shielded by the catheter.

It will also be appreciated that if the second tubular member is adapted to couple with a penetrating member and the jaws a safety sheath, the penetrating member and safety sheath can be attached to the handle and passed through a separate portal sleeve so that the penetrating member is retracted into the safety sheath and both the safety sheath and the penetrating member can be removed together with the handle maintaining the tip of the penetrating member in a protected condition within the sheath and leaving the separate portal sleeve in place within the wall of an anatomical cavity to form a portal for the introduction of medical instruments and/or fluids.

The modified handle 360 illustrated in FIG. 26 is similar to the handle 264 shown in FIG. 21 but with a pistol grip 362 secured to the bottom wall 323 of the handle housing and a pair of plugs 364 and 366 adapted to fit within the openings 368 and 370 in the first and second end walls 268 and 270, respectively. Pistol grip 362 is pivotally mounted on a post 372 projecting downward from a plate 374 secured to the bottom wall 323 of the handle housing 266. Handle grip 362 extends at an angle relative to the plate and is locked in a plurality of pivoted positions relative to the post by a pair of ball detents 376 and 378 extending from opposite sides of the post and engaging mating structure within the handle grip such that the handle grip can be manually rotated from one position to another to selectively utilize opposite ends of the handle for holding medical instruments. Plugs 364 and 366 each have a hollow cylindrical portion 380 configured to fit snugly within openings 368 and 370 formed in the first and second end walls 268 and 270, and a round flange 382 at one end of the hollow cylindrical portion to close the cylindrical portion and abut the end walls of the housing while providing a graspable rim for removing the plugs. When inserted into openings 368 and 370, plugs 364 and 366 operate to seal the handle housing 266 thereby preventing contamination of the interior of the housing during storage and also providing means for capping the handle after use to protect medical personnel from any body fluids or tissue introduced into the handle during a procedure. The handle 360 of FIG. 26 is also shown with outer ends of the first and second tubular members 274 and 276 and opposite ends of the rail member 272 having recesses 384 which define female portions of a detent coupling structure for detachably mating with protruding male portions formed at the proximal end of a medical instrument, such as the male detents 386 shown on the instrument 388 illustrated in FIG. 27. As shown, any medical instrument mated with the detents in the second cylindrical portion 390 of the rail member 272 will be moved along with the rail member and the second tubular member 276 toward the first end 268 of the housing when the handle is triggered. In FIG. 28, however, the second cylindrical portion 390 abuts the second end wall 270 of the housing and any medical instrument mounted within opening 374 is held stationary by engagement with detents 384 formed in the second end wall while the rail member 272 and the second tubular member 276 are moved toward the first end wall 268 of the housing.

From the above, it will be appreciated that the universal handle of the present invention can hold any type of medical instrument having a proximal end configured to mate with a mounting member of the universal handle or by use of adapters that couple the proximal ends of the instruments with mounting members of the handle. By "mounting member" is meant any handle component or combination of components having a configuration to mount a medical instrument, including but not limited to the housing recesses, jaws, rail members and tubular members disclosed herein. The universal handle can retract or extend a medical instrument relative to the housing and/or another medical instrument, for example to shield the distal end of a medical instrument such as a penetrating member after the wall of an anatomical cavity has been penetrated. Additionally, the universal handle of the present invention permits development of a modular system whereby, for example, medical personnel can match medical instruments with an appropriate handle having a desired characteristic, such as a retracting or extending force or power, to suit the particular procedure being performed. Use of the universal handle also reduces waste and minimizes the exposure of medical personnel to body fluids and the like by facilitating disposal of exhausted medical instruments and reuse of the universal handle with new medical instruments, thereby reducing cost and simplifying sterilization procedures as well. It will also be appreciated that by combining retracting and extending mechanisms in one universal handle the number of parts required for performing retracting and extending functions can be reduced and the efficiency of medical personnel can be increased by reducing the number of handles from which medical personnel must choose in order to obtain one or both of a retracting and extending function.

When both retracting and extending mechanisms are provided in a single handle, they can be coupled with mounting members on opposite sides of the handle, as shown, allowing medical personnel to select a side of the handle corresponding to the desired function, or the retracting and extending mechanisms can be coupled with mounting members on a single side of the universal handle for retracting one member while extending the other. Various mechanisms that can be simply modified to achieve retraction and extension of medical instruments from a single side of a universal handle of the present invention are disclosed in applicant's pending applications Ser. No. 08/279,170 and 08/279,172 filed Jul. 22, 1994, the disclosures of which are incorporated herein by reference.

The components of the universal safety handle of the present invention can be made of any suitable, medical grade material to permit sterilization for reuse or for single patient use. The components can be made of multiple parts of various configurations and materials to reduce cost. Furthermore, various valves, stopcocks and seals can be mounted within the housing to control fluid flow through the various mounting members, and conventional electrical connectors can be mounted on the handle and coupled with members of the handle to perform electrosurgery such as cautery and cutting.

The mounting members of the universal handle can have any configuration for mating with the proximal ends of medical instruments to be carried, including threaded or smooth projecting portions or nubs, conventional detent structures, sockets or collars, opposed jaws, Luer locks and/or any other type of coupling mechanism so long as the medical instruments can be easily attached to the mounting members for use and detached when exhausted. Preferably, proximal ends of the medical instruments are covered during use and accessible for being detached following use in order to provide an uncontaminated surface for being grasped when the instruments are to be removed. The mounting members of the universal handle can be configured to hold medical instruments in fixed positions relative to the handle housing or to permit movement of the instruments in response to forces acting on the medical instruments. Thus, for example, retaining portions of the jaws or rail members disclosed herein can be spring-biased to permit proximal and/or distal movement of the medical instruments mounted therein as desired. When jaws are provided for mounting the proximal end of a medical instrument, such as a cannula, bias springs, detent mechanisms, ring collars or any other suitable mechanisms can be used to draw and/or latch the jaws together around the medical instrument to hold or clamp the medical instrument while a second medical instrument, such as a needle disposed within a cannula, is retracted. Although two jaws are shown and described herein for mounting a medical instrument, it will be appreciated that any number of jaws having cooperating or opposed surfaces for retaining a medical instrument can be used.

The rail members can have various configurations to be engaged by the latch and released by operation of the trigger. Preferably, the rail members will have a configuration to serve as a stop or abutment for the operating member as exemplified herein by the U-shaped portions of the various rail members. When knobs are provided for manually moving the various members within the housing, the knobs can be coupled with the members directly or via any rail members mounting the members. Indicator strips can also be attached to the knobs in a manner to be visible through slots in the housing through which the knobs protrude. The indicator strips can be color coded and/or provided with other markings to indicate the position of the members to which the knobs are attached.

Release of the locking mechanisms can be triggered by movement of an operating member carried on any member of the universal handle movable in response to a reduction in force acting on the member, such as when a penetrating instrument carried by the handle enters an anatomical cavity. As described above, operating members are carried by one or more of the mounting members movable within the handle housing to limit the number of components in the handle; however, operating members could be carried on additional members movable in response to a reduction in force acting on the additional members such as, for example, a probe or rod in or alongside one of the mounting members and biased to protrude from the handle housing and/or a medical instrument carried by the housing.

The locking and releasing mechanisms require only a latch for locking the rail member in retracted or extended positions and a trigger for releasing the latch in response to distally biased movement of the operating member; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing in various ways to minimize the length of the housing and, therefore, the overall length of the handle. Various locking and releasing mechanisms that can be simply modified for use in the handle of the present invention are disclosed in applicant's pending applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868,566 and Ser. No. 07/868,578, filed Apr. 15, 1992, Ser. No. 07/929,338, filed Aug. 14, 1992, Ser. No. 07/845,177, filed Sep. 15, 1992, Ser. No. 07/945,177, filed Sep. 15, 1992, Serial No. 08/079,586, filed Jun. 22, 1993, Ser. No. 08/195,512, filed Feb. 14, 1994, Ser. No. 08/196,029, filed Feb. 14, 1994, Ser. No. 08/196,027, filed Feb. 14, 1994, Ser. No. 08/195,178, filed Feb. 14, 1994, Ser. No. 08/237,734, filed May 4, 1994, Ser. No. 08/247,205, filed May 20, 1994, Ser. No. 08/254,007, filed Jun. 3, 1994 and Ser. No. 08/260,439, filed Jun. 15, 1994, the disclosures of which are incorporated herein by reference. The above applications disclose automatically retracting safety penetrating instruments such that modification of the locking and releasing mechanisms requires configuring the latches to lock a rail member in a retracted or extended position. The above applications also disclose various bias arrangements useful with the handle of the present invention. Other locking and releasing mechanisms that can be used in the handle of the present invention are disclosed in applicant's pending applications Ser. Nos. 08/279,170 and 08/279,172 filed Jul. 22, 1994.

One or more control buttons such as the control buttons described in applicant's copending patent application Ser. No. 08/083,220, filed Jun. 24, 1993 can be mounted next to any latch for manually disengaging the latch to prevent locking of the handle in the loaded position. In addition, any latch arm or separate spring can carry a secondary pawl or latch at one end for locking a movable member in an extended or retracted position and can then be released by use of a control button as described above. It will thus also be appreciated that the movable members of the universal handle of the present invention can be locked in fixed positions to permit use of the instruments without any movement relative to the handle.

The various features of the disclosed embodiments can be combined dependent upon the medical instruments to be carried and the procedure to be performed with a particular universal handle.

Inasmuch as the present invention is subject to many variations, modifications and changes in detail, it is intended that all subject matter discussed or shown in the accompanying drawings be interpreted as illustrative only and not be taken in a limiting sense.

What is claimed is:

1. A universal handle for medical instruments comprising
a housing having a proximal end and a distal end;
a first mounting member disposed within said housing for detachably mounting a first medical instrument, said first mounting member being movable with the first medical instrument relative to said housing between an extended position proximate said distal end of said housing and a retracted position proximate said proximal end of said housing;
retracting means for moving said first mounting member proximally relative to said housing with the first medical instrument from said extended position to said retracted position;
locking means for engaging said first mounting member in said extended position to prevent said retracting means from moving said first mounting member into said retracted position; and
releasing means including an operating member movable distally in response to a reduction in force acting on a component of said handle for triggering release of said locking means to permit said retracting means to move said first mounting member proximally relative to said housing with the first medical instrument from said extended position to said retracted position.

2. A universal handle as recited in claim 1 and further comprising means for detachably mounting a second medical instrument on said housing.

3. A universal handle as recited in claim 2 wherein said means for detachably mounting a second medical instrument includes a pair of opposed jaws extending from a distal end of said housing.

4. A universal handle as recited in claim 3 wherein said jaws are pivotally attached to said housing and biased toward one another.

5. A universal handle as recited in claim 4 wherein said opposed jaws define a bore in axial alignment with an opening formed at said distal end of said housing to permit passage of the first medical instrument while preventing proximal movement of the second medical instrument.

6. A universal handle as recited in claim 5 wherein said opposed jaws are configured to engage a proximal end of the second medical instrument.

7. A universal handle as recited in claim 6 wherein said opposed jaws define an annular recess therebetween for receiving the proximal end of the second medical instrument.

8. A universal handle as recited in claim 2 wherein said first mounting member is configured to mount a penetrating member and said means for detachably mounting a second medical instrument is configured to mount a cannula.

9. A universal handle as recited in claim 1 wherein said first mounting member includes a distal end configured to mate with a proximal end of the first medical instrument.

10. A universal handle as recited in claim 9 wherein said distal end of said first mounting member includes a nub configured to be frictionally received within a recess formed in the proximal end of the first medical instrument.

11. A universal handle as recited in claim 9 wherein said distal end of said first mounting member is threaded to engage threads formed at the proximal end of the first medical instrument.

12. A universal handle as recited in claim 9 wherein said distal end of said first mounting member includes detents for engaging mating detent structure at the proximal end of the first medical instrument.

13. A universal handle as recited in claim 1 wherein said locking means permits a predetermined amount of proximal movement of said first mounting member away from said extended position in response to a proximal force acting on a distal end of said first mounting member and further comprising bias means for biasing said first mounting member distally toward said extended position.

14. A universal handle as recited in claim 13 and further comprising a rail member disposed within said housing and having forward and rearward walls, said rail member being movable within said housing between an extended position proximate said distal end of said housing and a retracted position proximate said proximal end of said housing, wherein said first mounting member includes a cylindrical body extending distally through an opening in said forward wall of said rail member and a flange disposed at a proximal end of said cylindrical body between said forward and rearward rail member walls and wherein said locking means engages said rail member to lock said first mounting member.

15. A universal handle as recited in claim 14 wherein said bias means includes a spring biasing said flange distally toward said forward wall of said rail member.

16. A universal handle as recited in claim 15 and further comprising a knob coupled with said first mounting member for manually moving said first mounting member distally from said retracted position to said extended position.

17. A universal handle as recited in claim 16 wherein said operating member is formed by said flange.

18. A universal handle for medical instruments comprising a housing having proximal and distal ends;
a first mounting member disposed within said housing for detachably mounting a first medical instrument, said first mounting member being movable with the first medical instrument relative to said housing between a retracted position proximate said proximal end of said housing and an extended protruding position proximate said distal end of said housing;
extending means for moving said first mounting member distally relative to said housing with the first medical instrument from said retracted position to said extended protruding position;
locking means for engaging said first mounting member in said retracted position to prevent said extending means from moving said first mounting member into said extended position; and
releasing means including an operating member carried by a component of said handle for triggering release of said locking means in response to a reduction in force acting on said component so as to permit said extending means to move said first mounting member distally relative to said housing with the first medical instrument from said retracted position to said extended position.

19. A universal handle as recited in claim 18 and further comprising a second mounting member disposed within said housing for detachably mounting a second medical instrument, said second mounting member being movable with the second medical instrument between an extended rest position proximate said distal end of said housing and a retracted position proximate said proximal end of said housing, and bias means for distally biasing said second mounting member toward said rest position, wherein said operating member is carried by said second mounting member.

20. A universal handle as recited in claim 19 wherein a distal end of said first mounting member includes a receptacle configured to receive a proximal end of the first medical instrument.

21. A universal handle as recited in claim 20 and further comprising a pair of opposed jaws extending from a distal end of said housing, wherein said receptacle is disposed for sliding movement between said opposed jaws.

22. A universal handle as recited in claim 21 wherein said jaws are pivotally attached to said housing and biased toward one another to define a passage for guiding said receptacle and for preventing the first medical instrument from becoming dislodged from said receptacle.

23. A universal handle as recited in claim 19 wherein said locking means permits a predetermined amount of proximal movement of said second mounting member away from said extended rest position in response to a proximal force acting on a distal end of said second mounting member and further comprising bias means for biasing said second mounting member distally toward said extended position.

24. A universal handle as recited in claim 19 wherein said first mounting member includes a rail member having forward and rearward walls disposed within said housing and a cylindrical portion extending through an opening at said distal end of said housing to form a receptacle for receiving the proximal end of the first medical instrument, wherein said second mounting member includes a cylindrical body extending distally through an opening in said forward wall of said rail member and a flange disposed at a proximal end of said cylindrical body between said forward and rearward rail member walls and further comprising a stop limiting distal movement of said second mounting member relative to said housing.

25. A universal handle as recited in claim 24 wherein said bias means includes a spring biasing said flange distally toward said forward wall of said rail member.

26. A universal handle as recited in claim 25 and further comprising a knob coupled with said first mounting member for manually moving said first mounting member proximally from said extended position to said retracted position.

27. A universal handle as recited in claim 18 wherein a distal end of said first mounting member is threaded.

28. A universal handle as recited in claim 18 wherein a distal end of said first mounting member includes detents.

29. A universal handle as recited in claim 18 wherein said second mounting member includes a distal end configured to mate with a proximal end of the second medical instrument.

30. A universal handle as recited in claim 29 wherein said distal end of said second mounting member includes a nub.

31. A universal handle as recited in claim 29 wherein said distal end of said second mounting member is threaded.

32. A universal handle as recited in claim 29 wherein said distal end of said second mounting member includes detents.

33. A universal handle for medical instruments comprising a housing having first and second opposed ends;

mounting means movably disposed within said housing and having first and second opposed ends, said first end of said mounting means having a configuration to mount a first medical instrument from said first end of said housing, said second end of said mounting means having a configuration to mount a second medical instrument from said second end of said housing, said mounting means being movable relative to said housing between a first position proximate said first end of said housing and a second position proximate said second end of said housing:

bias means for biasing said mounting means toward said first end of said housing;

locking means for locking said mounting means in said second position; and releasing means including an operating member carried by a component of said handle for triggering release of said locking means in response to a reduction in force acting on said component so as to permit said bias means to move said mounting means toward said first end of said housing.

34. A universal handle as recited in claim 33 and further comprising a pair of opposed jaws extending from said second end of said housing.

35. A universal handle as recited in claim 34 wherein said jaws are pivotally attached to said housing and biased toward one another.

36. A universal handle as recited in claim 34 wherein said opposed jaws are configured to engage a proximal end of a fourth medical instrument from said second end of said housing.

37. A universal handle as recited in claim 33 wherein said first end of said mounting means is threaded.

38. A universal handle as recited in claim 33 wherein said first end of said mounting means includes detents.

39. A universal handle as recited in claim 33 wherein said first end of said mounting means includes a nub.

40. A universal handle as recited in claim 33 wherein said second end of said mounting means is configured to mate with a proximal end of the second medical instrument.

41. A universal handle as recited in claim 40 wherein said second end of said mounting means includes a nub.

42. A universal handle as recited in claim 40 wherein said second end of said mounting means is threaded.

43. A universal handle as recited in claim 40 wherein said second end of said mounting means includes detents.

44. A universal handle as recited in claim 33 and further comprising removable plugs for sealingly engaging openings in said first and second ends of said housing to cover said first and second ends of said mounting means.

45. A universal handle as recited in claim 33 and further comprising an adapter having a proximal end configured to detachably mount at least one of said first and second ends of said mounting means and a distal end configured to detachably mount the proximal end of a medical instrument.

46. A universal handle as recited in claim 45 wherein said adapter is at least partly solid to form a barrier preventing fluid flow into said housing when mounted on one of said first and second ends of said mounting means.

47. A universal handle for medical instruments as recited in claim 33 wherein said mounting means includes a first mounting member disposed within said housing and having first and second opposed ends, said first end of said first mounting member having a configuration for mounting the first medical instrument from said first end of said housing, said first mounting member being movable between a rest position proximate said first end of said housing and a retracted position proximate said second end of said housing; and a second mounting member disposed within said housing and having first and second opposed ends, said second end of said second mounting member having a configuration for mounting the second medical instrument from said second end of said housing, said second mounting member being movable between an extended position proximate said second end of said housing and a retracted position proximate said first end of said housing.

48. A universal handle as recited in claim 47 wherein said first and second mounting members slidingly engage one another.

49. A universal handle as recited in claim 47 and further comprising a rail member movably disposed within said housing, said rail member mounting said first and second mounting members.

50. A universal handle as recited in claim 49 wherein said rail member has first and second walls and said first and second mounting members each include a flange disposed between said first and second walls of said rail member.

51. A universal handle as recited in claim 50 and further comprising bias means for urging said flanges of said first and second mounting members away from one another and toward opposite ends of said rail member.

52. A universal handle as recited in claim 51 wherein said locking means engages said rail member in a loaded position where said first mounting member is in said retracted position and said second mounting member is in said extended position.

53. A universal handle as recited in claim 52 and further comprising handle means coupled with said rail member for manually moving said rail member into said loaded position.

54. A universal handle as recited in claim 53 and further comprising a stop limiting movement of said first mounting member toward said first end of said housing and wherein said rail member has a first end configured for mounting a third medical instrument from said first end of said housing.

55. A universal handle as recited in claim 54 wherein said first and second mounting members each carry an operating member for engaging said releasing means to release said locking means to allow said bias means to move said first and second mounting members toward said first end of said housing.

56. A universal handle as recited in claim 54 wherein said first end of said rail member includes a receptacle configured to receive a proximal end of the third medical instrument.

57. A universal handle as recited in claim 56 and further comprising opposed jaws extending from said first end of said housing, wherein said receptacle is disposed for sliding movement between said opposed jaws.

58. A universal handle as recited in claim 57 wherein said opposed jaws are pivotally attached to said housing and biased toward one another to define a bore for guiding said receptacle and for preventing the first medical instrument from becoming dislodged from said receptacle.

59. A universal handle as recited in claim 54 wherein said first and second mounting members are configured to mount penetrating members and said first end of said rail member is configured to mount a cannula.

\* \* \* \* \*